United States Patent
Hibri

(10) Patent No.: US 10,653,550 B2
(45) Date of Patent: May 19, 2020

(54) EXTERNAL PENILE ERECTION SYSTEM

(71) Applicant: Nadi S. Hibri, San Antonio, TX (US)

(72) Inventor: Nadi S. Hibri, San Antonio, TX (US)

( * ) Notice: Subject to any disclaimer, the term of this patent is extended or adjusted under 35 U.S.C. 154(b) by 269 days.

(21) Appl. No.: 15/895,299

(22) Filed: Feb. 13, 2018

(65) Prior Publication Data

US 2018/0228639 A1    Aug. 16, 2018

Related U.S. Application Data

(60) Provisional application No. 62/458,120, filed on Feb. 13, 2017.

(51) Int. Cl.
*A61F 5/41*    (2006.01)

(52) U.S. Cl.
CPC .......... *A61F 5/41* (2013.01); *A61F 2005/411* (2013.01); *A61F 2005/412* (2013.01); *A61F 2005/414* (2013.01); *A61F 2005/415* (2013.01)

(58) Field of Classification Search
CPC .......... A61F 5/41; A61F 2005/411–415; A61F 2/0054; A61H 19/32
USPC .......................................................... 600/39
See application file for complete search history.

(56) References Cited

U.S. PATENT DOCUMENTS

| | | | |
|---|---|---|---|
| 3,495,589 A * | 2/1970 | Clement | A61F 5/41 600/38 |
| 3,820,533 A | 6/1974 | Jones | 600/38 |
| 4,378,008 A | 3/1983 | Osbon | |
| 4,407,275 A | 10/1983 | Schroeder | |
| 4,641,638 A | 2/1987 | Perry | 600/39 |
| 4,723,538 A | 2/1988 | Stewart | |
| 4,741,329 A | 5/1988 | Marcune | 600/41 |
| 4,753,227 A | 6/1988 | Yanuk, Jr. | 600/41 |
| 4,856,498 A | 8/1989 | Osbon | 600/38 |
| 4,895,140 A * | 1/1990 | Bellak | A61F 5/41 600/39 |
| 5,125,890 A | 6/1992 | Merrill et al. | 600/39 |
| 5,295,946 A * | 3/1994 | Collins | A61F 5/41 600/41 |
| 5,344,389 A | 9/1994 | Walsdorf et al. | 600/41 |
| 5,964,695 A | 10/1999 | Vollrath et al. | 600/38 |
| 6,659,938 B1 | 12/2003 | Orlowski et al. | |
| 7,377,896 B2 | 5/2008 | Dykers | |

(Continued)

OTHER PUBLICATIONS

First Office Action in copending U.S. Appl. No. 15/895,862, dated Feb. 4, 2020, 12-pgs.

*Primary Examiner* — Catherine B Kuhlman
(74) *Attorney, Agent, or Firm* — Blank Rome LLP

(57) ABSTRACT

A system for affecting, augmenting, or enhancing erection of the penis includes an elastomeric sleeve designed to comfortably and securely encircle the base of the penis. The sleeve is provided with a pair of inflatable chambers, a dorsal insert, and a ventral insert which are configured to apply focal pressure on the dorsal penile veins, while avoiding undue constriction of the corpora cavernosa or compression of the urethra, dorsal penile arteries, or nerves. The system includes fluid transfer apparatus having a reservoir for pressurized fluid, a pump, and valves for controlling the flow of fluid to the inflatable chambers. The system also includes an inflatable sealing apparatus which, when used in combination with a conventional vacuum erection tube, forms an airtight seal between the sleeve and the open end of the inflatable sealing member.

18 Claims, 26 Drawing Sheets

(56) References Cited

U.S. PATENT DOCUMENTS

| | | | |
|---|---|---|---|
| 2003/0136415 A1* | 7/2003 | Lanton, Jr. | A61F 5/41 128/842 |
| 2014/0171734 A1* | 6/2014 | Kassman | A61H 19/50 600/38 |
| 2016/0296362 A1 | 10/2016 | Suarez | |

* cited by examiner

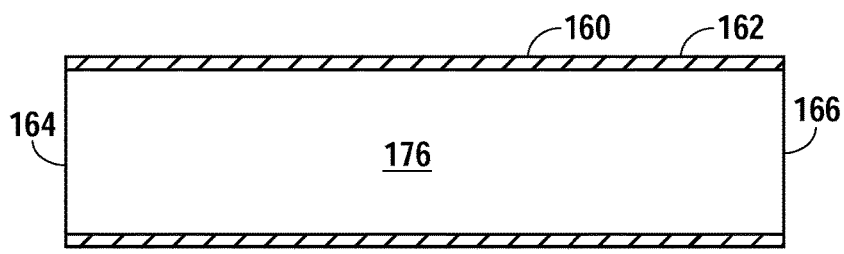 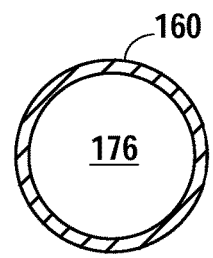
Fig. 8A    Fig. 8B
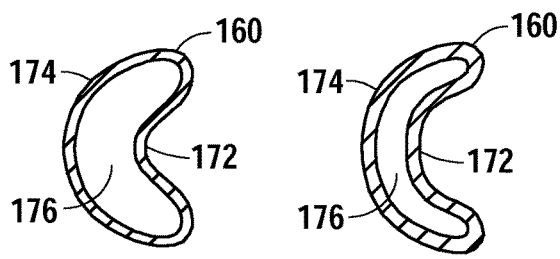 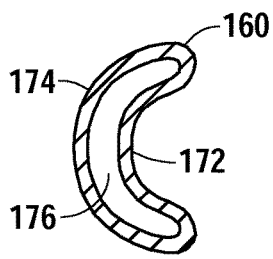 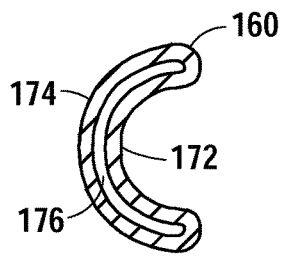 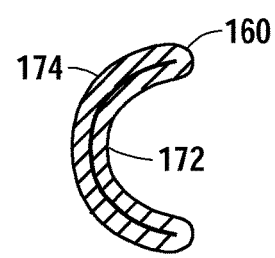
Fig. 8C    Fig. 8D    Fig. 8E    Fig. 8F
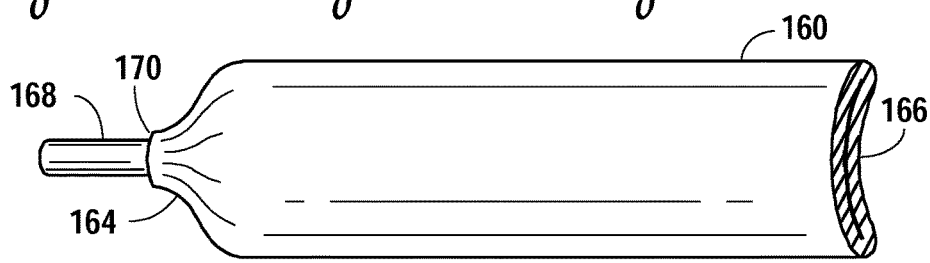
Fig. 8G
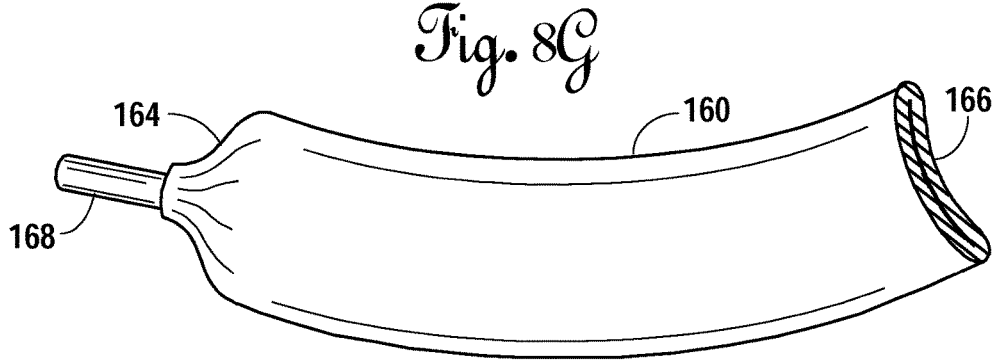
Fig. 9

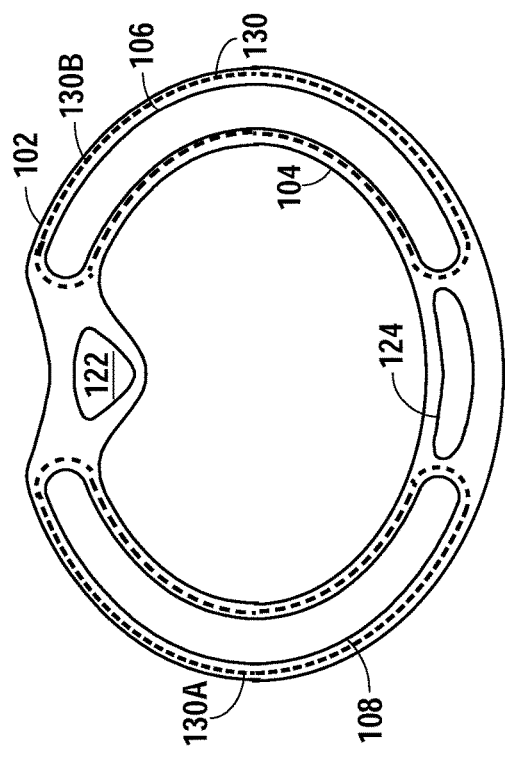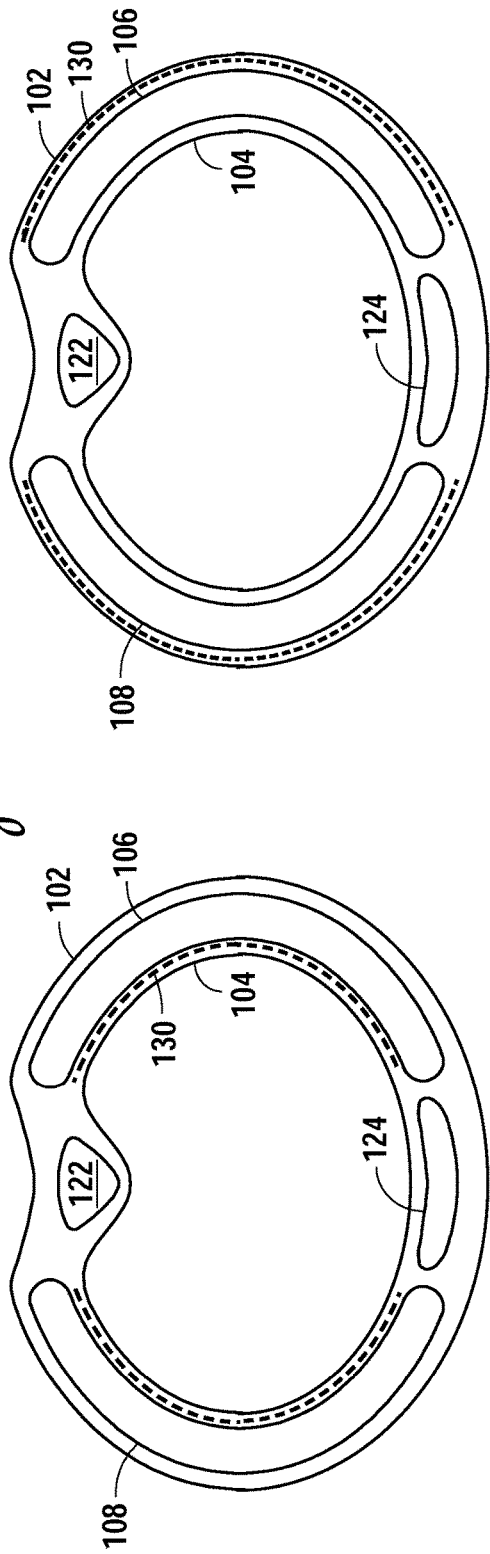

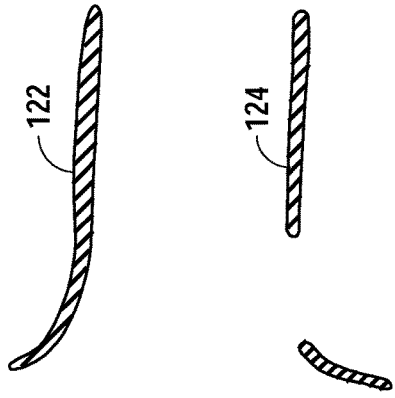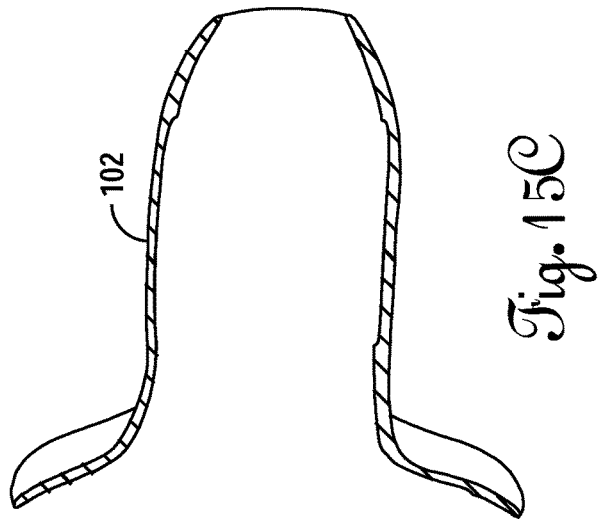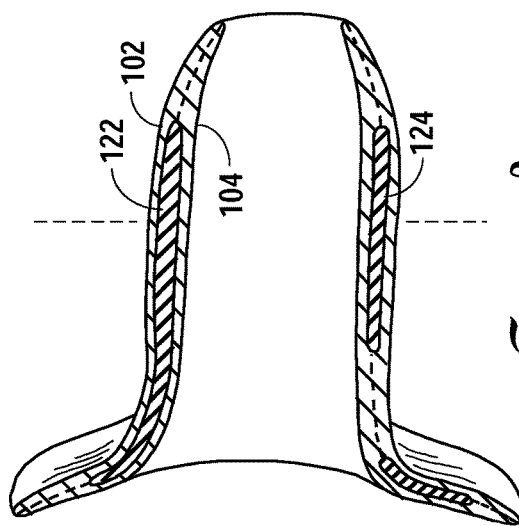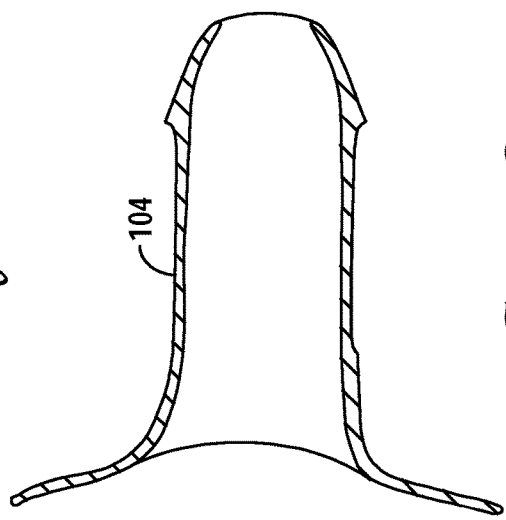

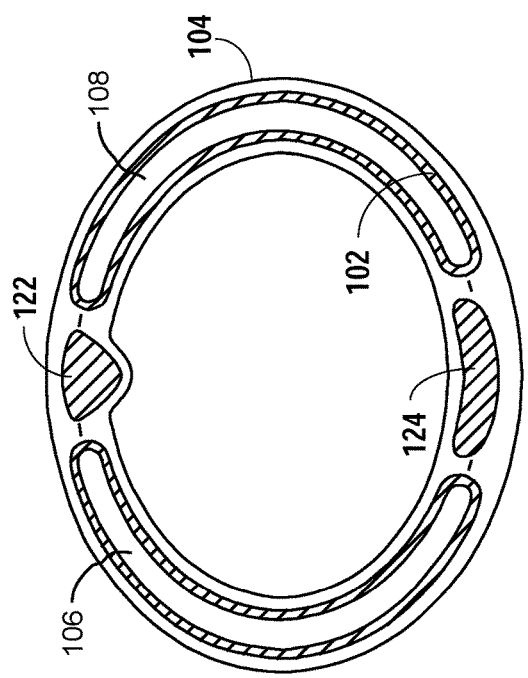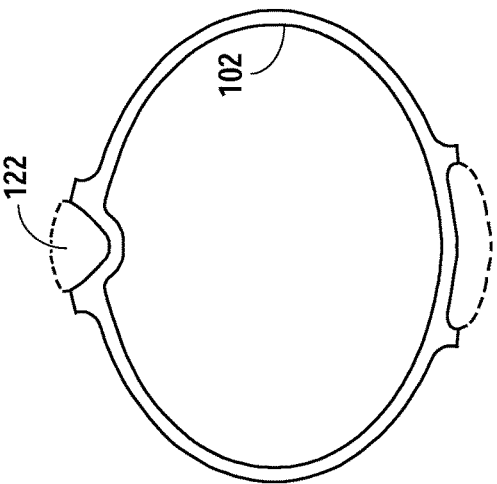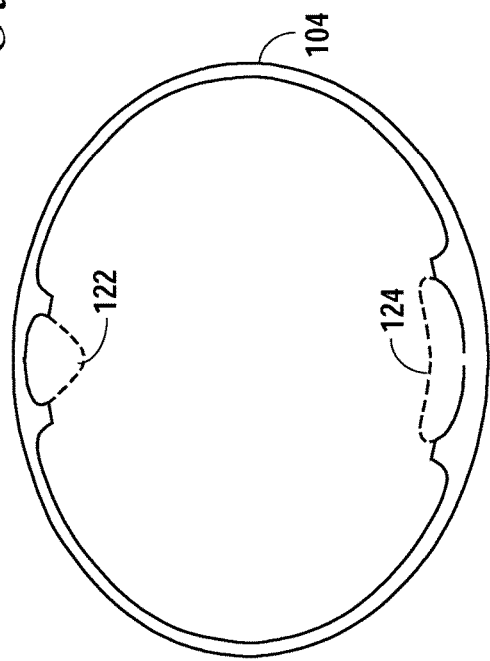

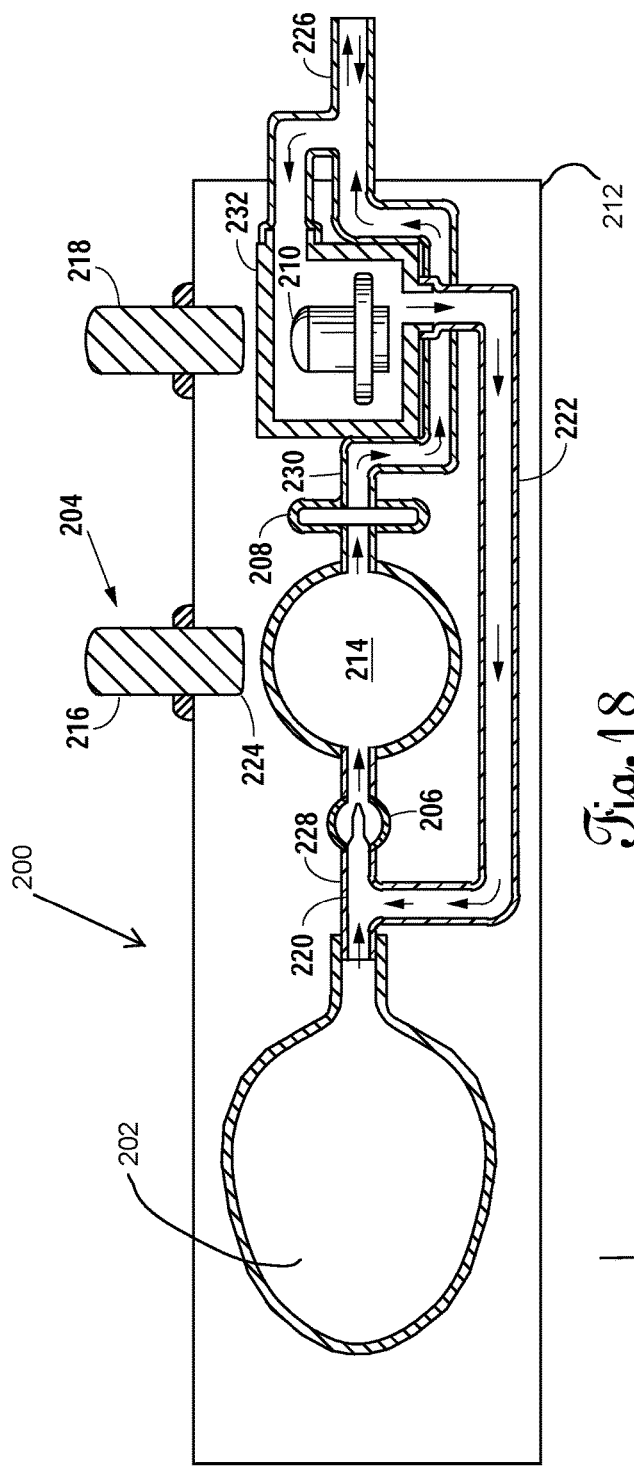
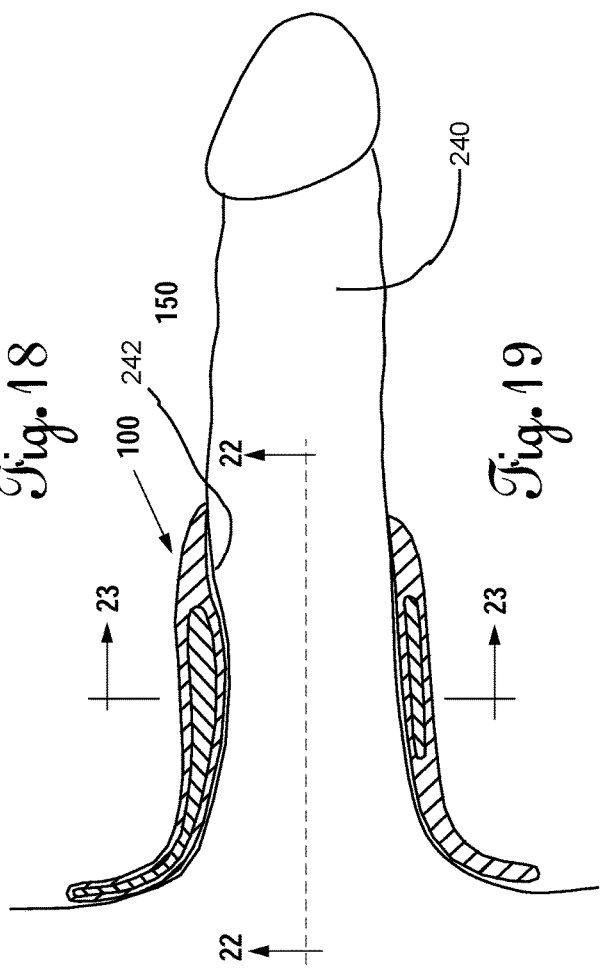
Fig. 18
Fig. 19

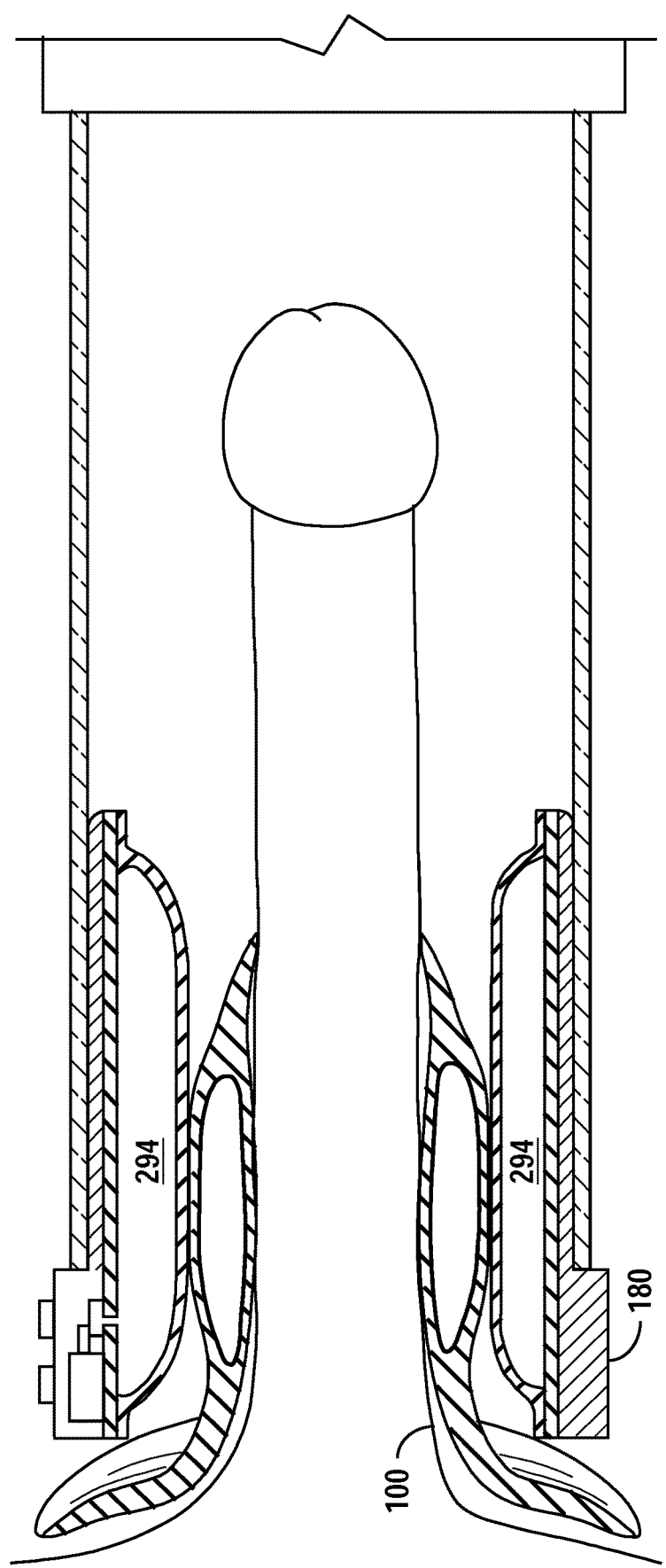

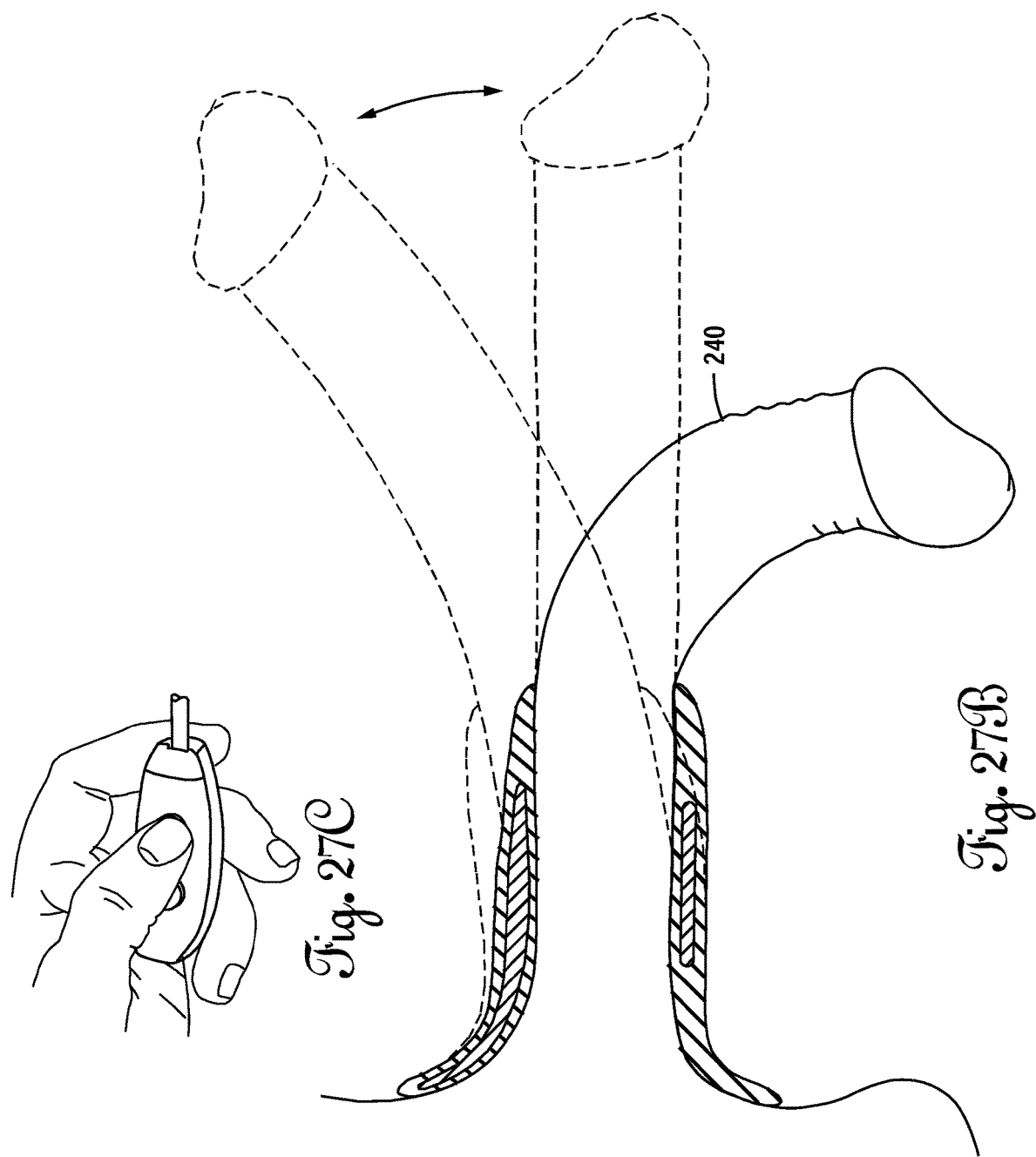

EXTERNAL PENILE ERECTION SYSTEM

CROSS-REFERENCE TO RELATED APPLICATIONS

This application claims priority to U.S. Provisional Application No. 62/458,120 filed Feb. 13, 2017, the entire contents of which is specifically incorporated by reference herein without disclaimer.

FIELD OF THE INVENTION

The present invention relates generally to erection aids and more specifically to vacuum-constriction erection aid devices used to induce and maintain erection in males having erectile dysfunction.

BACKGROUND OF THE INVENTION

In some instances of erectile dysfunction, in which the patient does not respond to more conventional therapy, the surgical implantation of a penile prosthesis was considered the only practical means of remedying the dysfunction. In the past, several types of penile prostheses have been employed. One type of penile implant prosthesis which has been used includes a pair of inflatable and distensible tubes that are implanted into the corpora cavernosae of the penis. Typically, each of the tubes is connected by tubing to a fluid filled reservoir through a pump and valve assembly. The entire system is typically surgically implanted in the body of the patient. A second type is a rod of suitable stiffness surgically implanted into the corpus cavernosus of the penis.

Most males find the surgical option intimidating. The surgical prior art solutions have proven undesirable and generally do not provide a popular or reliable solution to the erectile dysfunction of most patients.

External erection control systems have also been developed that typically provide vacuum-constriction therapy. Most vacuum-constriction devices have three essential components—a cylindrical penile vacuum chamber, a vacuum pump, and some form of constriction band, clip device or male truss. There have been numerous modifications and variations of these devices. However, existing vacuum constriction devices have substantial drawbacks and deficiencies which make them unacceptable to many users.

Problems of design and function pertinent to prior devices include the lack of means for effectively creating an airtight seal between the vacuum chamber with the penis or with the abdominal wall around the penis. Moreover, conventional constriction bands, rings, sleeves, or sealing diaphragms are not adaptable to conform to the users penile anatomy or apply the appropriate degree of pressure or constriction for a particular users groin. Another deficiency of some of these devices is that extraneous skin of the scrotum is often drawn into the chamber by the vacuum if the device is carelessly applied. Another disadvantage of prior art vacuum-constriction devices is that they are difficult to operate and some require the user to perform two separate operations to transfer the constriction band from the vacuum chamber to the penis and simultaneously relieve the vacuum within the chamber. Conventional bands become twisted and entangled, are often too tight and painful to apply and remove. Furthermore, conventional bands cause undue constriction and deflation of the underlying corpora cavernosa, diminishing the rigidity of the base of the penis at this level, making sexual intercourse difficult. The root of the penis, which extends inwardly of the groin of the individual, remains flaccid proximal to a conventional constriction ring and the penis does not achieve and maintain a natural erection position.

Current body shields in use are placed over the penis against the body as a guard between a vacuum erection device and the scrotum. The shields protect the skin and pubic hair from getting pulled while using the pump.

There have been attempts in the past to address deficiencies with erectile aids. U.S. Pat. No. 5,344,389 Walsdorf describes a combination seal and constricting device to be used with a conventional vacuum erection device. The device is positioned at the open end of the evacuation cylinder of a conventional vacuum erection device with the radially extending skirt flush between the open end of the cylinder and the users groin. In this position, the subject device aids in establishing and maintaining a substantially airtight seal around the open end of the cylinder and the base of the penis during evacuation pumping. U.S. Pat. No. 5,125,890 to Merrill discloses a penile sealing diaphragm that forms an airtight seal between the tubular chamber and the penis. A constriction band dislodging mechanism comprises a flexible strap which is attached to the sealing diaphragm to provide a simple method for transferring any constriction band from the chamber onto the penis. U.S. Pat. No. 5,964,695 Vollrath describes a diaphragm seal that forms a substantially airtight seal along the constrictor ring. The erection device is provided as a kit containing a rigid vacuum tube, a hand or power operated pump, and several diaphragm seals and constrictor rings of various sizes to achieve a custom fit and optimum results.

Other options disclosed by the prior art involve insertion of the penis into a rigid sheath which is intended to provide the necessary mechanical support. However, this type of device suffers from being uncomfortable and ineffective. As a result, prior art external devices do not provide a viable option to the problems presented.

Accordingly, there exists a need in the art for an external penile erection system that is biomimetic, non-surgical, affordable, and provides sexual satisfaction to both partners.

SUMMARY OF THE INVENTION

It is a general object of the present disclosure to provide a novel, pressurizable penile erection system which is wearable, readily controllable, and which users will like to use.

It is a further object of the present disclosure to disclose a penile sleeve which can be applied to the base of the penis and controllably expanded with fluid to selectively compress the dorsal penile veins while avoiding undue constriction of the corpora cavernosa or compression of the urethra or dorsal penile arteries and nerves.

It is a further object of the present disclosure to disclose a penile sleeve which, when used with an inflatable sealing apparatus, tends to draw the root of the penis into the penile sleeve so that a more natural erection is achieved and maintained after the vacuum tube is removed. Since a conventional type ring is not utilized to cause undue constriction of the corpora cavernosae, dorsal penile arteries and nerves, and urethra, the shaft, base, and root portions of the male genital are adequately distended to allow the penis to rise to a more natural erect position after the vacuum tube is removed.

In one embodiment, a penile sleeve comprises a centrally disposed collar portion that encircles the shaft of the penis, a proximal skirt portion adaptable to conform to the users groin, and a tapered elastic distal portion. The penile sleeve is constructed from an inner layer and an outer layer of soft elastomeric material such as silicone. Embedded in an intermediate layer of the penile sleeve are, a pair of arcuate balloons, a fiber matrix, and dorsal and ventral inserts. The distal portion of the penile sleeve may be tapered, stretchy, and compliant, and does not have an intermediate layer. The skirt portion of the penile sleeve includes a firm core element in the intermediate layer, integral with the dorsal insert of the cylindrical collar portion, configured to stabilize the cylindrical collar portion of the penile sleeve firmly against the users groin.

In some embodiments, the paired arcuate balloons may be inflated and deflated and, when deflated, the penile sleeve is stretchable, having a relatively wide conduit to provide easy application and removal of the penile sleeve to the penis.

In some embodiments, inflation of the arcuate balloons causes the inner walls of the balloons to translate inwards to exert firm but even pressure on the side walls of the shaft and the distended corpora cavernosa to support the base of the penis during an erection. When the corpora cavernosa are firm and distended, during spontaneous erection or following vacuum suction, mechanical support is provided by the penile sleeve to the erect penis.

In still other embodiments, an insert is incorporated in the dorsal aspect of the penile sleeve. The dorsal insert is preferably made of an elastomeric material that is relatively non-compliant. Upon pressurized inflation of the arcuate chambers, an inner convex or wedge shaped margin of the insert provides biasing contact against the dorsal side of the penis to restrict blood flow in the dorsal veins, and thus initiating penile engorgement and erection.

In some embodiments, an insert is incorporated in the ventral aspect of the penile sleeve. The ventral insert is preferably made of a compliant or soft silicone material and is stretchy. It is shaped and configured to provide increased circumferential compliance to the sleeve and to avoid undue compression of the urethra to allow unrestricted ejaculation without the possibility of self-injury.

In some embodiments, the penile sleeve comprises a proximal skirt portion adaptable to conform to the users groin, having a firm core element integral with said dorsal insert to provide support and stabilization to the base of the penis.

In some embodiments, penile curvature control arrangements are provided. The components of the penile sleeve are configured to allow for differential compliance, differential expansion, and controlled curvature of the penile sleeve and the base of the penis therein. When the arcuate balloons are inflated to an expanded state, they assume a curved shape (e.g. banana shape) in the longitudinal plane. The curve shape of the resulting penile sleeve transmits a force to the penile shaft therein, thereby causing the shaft to bend.

In some embodiments, inflation of the arcuate balloons expands the penile sleeve inward and providing an airtight seal between the inner surface of the penile sleeve and the penis.

In some embodiments, the penile erection system includes a fluid transfer apparatus including a wearable inflation-deflation unit for supplying pressurizing fluid to the expandable penile sleeve, and a flexible tubing communicating between a reservoir chamber in the inflation-deflation unit and the arcuate chambers of the penile sleeve. The inflation-deflation unit includes an inflatable fluid reservoir, a pumping element, a flap valve, a check valve, and a pressure control valve; all compactly enclosed within a unit housing.

In some embodiments, the penile erection system includes an inflatable sealing apparatus having means for effectively creating an airtight seal between a tubular vacuum chamber and the penile sleeve. When used with a vacuum erection device, the apparatus aids in establishing and maintaining a substantially airtight seal around the open end of the device and the base of the penis during vacuum evacuation. The inflatable sealing apparatus is insertable within the inlet of a conventional vacuum erection tube or chamber.

In some embodiments, the present disclosure comprises a method of forming an inflatable sealing apparatus.

In some embodiments, a method of manufacturing the penile sleeve device is provided. The method of manufacturing may include various methods for manufacturing arcuate balloons, and methods for assembling components of the penile sleeve.

In some embodiments, a method of use to initiate and maintain erection of a penis is provided that comprises the steps of placing the disclosed penile sleeve into the inlet of the inflatable sealing apparatus, attached to a conventional vacuum erection device; placing the users flaccid or semi-flaccid penis into the aperture of the penile sleeve; creating an airtight seal between the inflatable sealing apparatus and the penile sleeve, and between the penile sleeve and the penis; activating the evacuation cycle of the vacuum erection device until the user has achieved the desired erect state; actuating the fluid transfer apparatus to pressurize the arcuate balloons of the penile sleeve to compress the dorsal penile veins; releasing the vacuum created by the evacuation cycle; and withdrawing the vacuum erection device and the inflatable sealing apparatus from the penile sleeve and the erect penis therein.

BRIEF DESCRIPTION OF THE FIGURES

FIG. 8A is a schematic cross-sectional view in the longitudinal plane of a tubular elastomeric precursor of the arcuate balloon shown in FIG. 8G.

FIGS. 8B, 8C, 8D, 8E, and 8F are schematic cross-sectional views taken in the axial plane of the tubular elastomeric precursor shown in FIG. 8A in different stages of deflation and formation of the outer curved wall and inner curved wall portions of arcuate balloon 8G.

FIG. 8G is a schematic perspective view in the longitudinal plane showing transformation of the tubular elastomeric precursor tube of FIG. 8A into an arcuate balloon;

FIG. 9 is a schematic perspective view similar to FIG. 8G in which inflation of the arcuate balloon has resulted in curvature of the balloon secondary to built-in differential compliance of the balloon wall;

FIGS. 10B, 10C, 10D, 10E, and 10F are cross-sectional views similar to FIG. 10A showing various embodiments of a fiber matrix 130 in the intermediate layer of a penile sleeve;

FIG. 15A is a cross-sectional view along the longitudinal plane of a penile sleeve similar to FIG. 1A;

FIGS. 15B, 15C, and 15D are cross-sectional views of disassembled components of the penile sleeve shown in FIG. 15A (the arcuate balloons are not visible in the midsagittal plane). FIG. 15B illustrates an inner silicone layer; FIG. 15C illustrates an outer silicone layer; and FIG. 15D illustrates dorsal and ventral inserts;

FIG. 16A is a cross-sectional view in the axial plane of the cylindrical collar portion of penile sleeve shown in FIG. 15A;

FIGS. 16B and 16C are cross-sectional views of disassembled components of the penile sleeve shown in FIG. 15A showing the outer and inner silicone layers;

FIG. 18 is a disassembled side elevational view in partial cross-sectional of one exemplary embodiment of an inflation-deflation unit of the fluid transfer apparatus of the present disclosure;

FIG. 19 is a schematic cross-sectional view in the sagittal plane showing the penile sleeve applied around the circumference of a flaccid human penis.

FIG. 26C is a top elevational view similar to FIG. 26B following continued application of vacuum pressure causing engorgement and enlargement of the penis into an erect state;

FIG. 27B is a side perspective view of a penile sleeve applied about the base of the penis showing a flaccid penis, semi-erect to fully erect state, with cephalad curvature of the penile sleeve and the erect penis therein as the arcuate balloons are pressurized activating the curvature control arrangement; and FIG. 27C is a side perspective view of the users hand holding the inflation-deflation unit of the fluid transfer apparatus as he activates the pump button and the pressure control button.

DETAILED DESCRIPTION

Turning now to the figures, reference numbers are used to designate corresponding elements in the figures. The figures, which are not necessarily to scale, depict selected embodiments. Although the present disclosure makes reference to exemplary embodiments, those skilled in the art will recognize that changes may be made in form and detail without departing from the scope and spirit of the invention. Examples of construction, materials, dimensions, and manufacturing process are provided for selective elements. As such, it is intended that the following detailed specification be regarded as illustrative rather than limiting, and that it is the appended claims, including all equivalents thereof, which are intended to define the scope of the invention.

Throughout this specification, the word "comprise" will be understood to imply the inclusion of a stated element, integer, or step, or group of elements, integers or steps, but not the exclusion of any other element, integer or step, or group of elements, or groups or steps.

In the present context, the term "dorsal" as used herein refers to the upper side of an organ such as the penis, as viewed by the user. The term "ventral" as used herein, refers to the underside of an organ such as the penis, as viewed by the user.

In the present application, the term "proximal" refers to the portion of the penile sleeve closest to the abdominal wall, while the term "distal" refers to the portion of the sleeve that is generally towards the tip of the penis.

The term "balloon" is used broadly throughout this disclosure to refer to a variety of inflatable medical devices having a variety of shapes, characteristics, and uses.

The term "balloon" is used specifically throughout this disclosure to refer to a tubular elastomeric membrane comprising a wall defining an interior portion of the balloon, and separating the interior portion from the external environment when one or both ends of the tubular membrane are sealed.

The term "arcuate balloon", refers to a balloon configuration formed when the interior portion of a tubular balloon is deflated, a lesser curvature portion of the balloon is displaced towards the interior portion beyond the central axis an arcuate chamber is formed which, in cross-section, takes the form of arcuate arcs of different widths depending on the degree of inflation of the arcuate chamber. When the interior space is completely empty, a potential arcuate interior space is created in which the lesser curvature portion is opposed to the greater curvature portion, forming two folded portions. This configuration may enable the arcuate balloon to be folded into a low profile design. Fluid may be introduced into the interior portion of an arcuate balloon, exerting pressure on and separating the inner and outer wall portions.

Figure 1A:
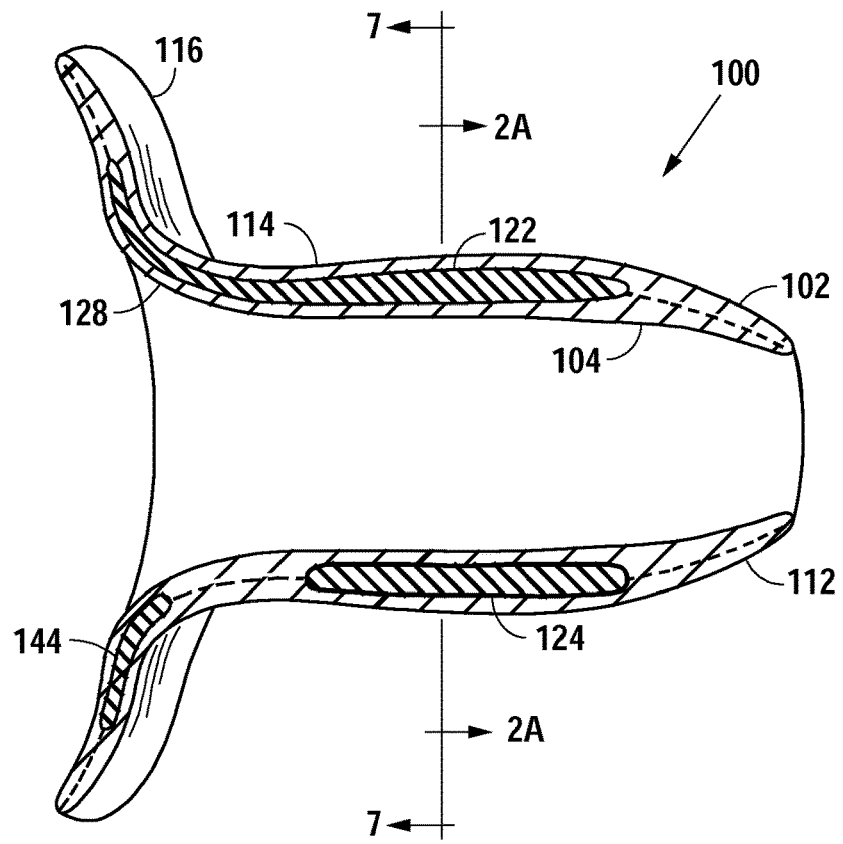
FIG. 1A is a cross-sectional view of an embodiment of a penile sleeve along a longitudinal plane.
Figure 1B:
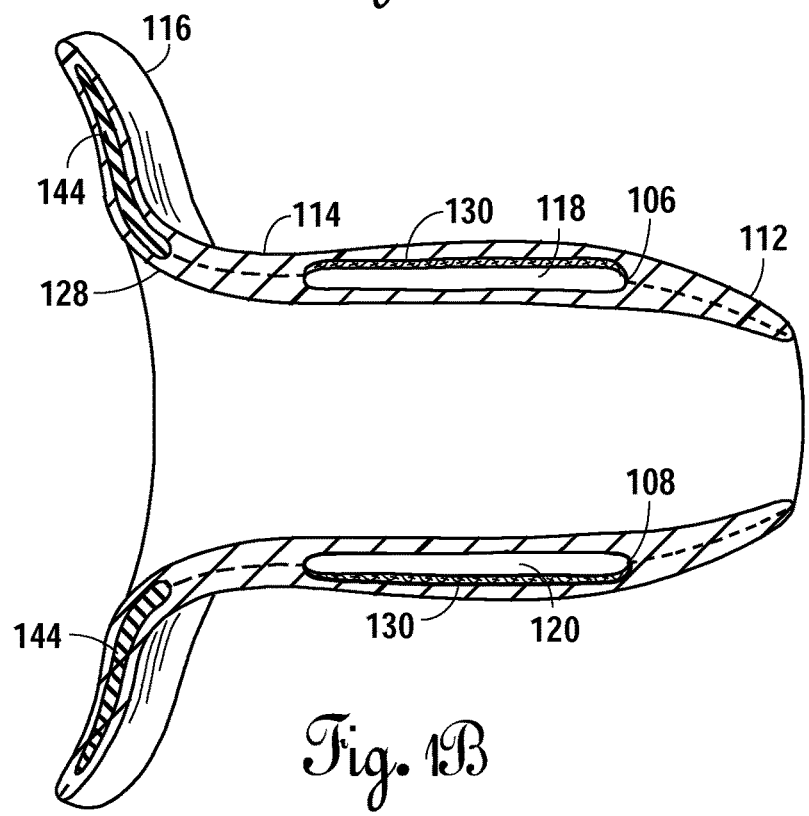
FIG. 1B is a cross-sectional view of the embodiment of the penile sleeve shown in FIG. 1A taken along a longitudinal plane orthogonal to the plane in FIG. 1A.

FIG. 1A is a partial cut away view in the longitudinal plane of penile sleeve 100 comprising a cylindrical portion 114, a flanged proximal portion in the form of a skirt 116, and a tapered distal portion 112.

Penile sleeve 100 comprises an inner layer 104 and an outer layer 102. Two generally symmetrically disposed arcuate balloons 106, 108 are positioned within the interior of the cylindrical portion 114 and forming two substantially fluid tight longitudinally extending arcuate chambers 118, 120. A fiber matrix 130 may be disposed between arcuate balloons 106, 108 and layers 104, 102. Fiber matrix 130 may be a woven or knitted fabric layer. As will be discussed in more detail below, fiber matrix 130 may be configured to provide a limited and predetermined degree of circumferential expansion to allow accommodation of penises of different sizes or states of erection. The fiber reinforced silicone material creates a soft yet semi-compliant structural configuration.

Distal portion 112 is preferably tapered, stretchy, and more compliant than the rest of cylindrical portion 114.

Figure 1C:
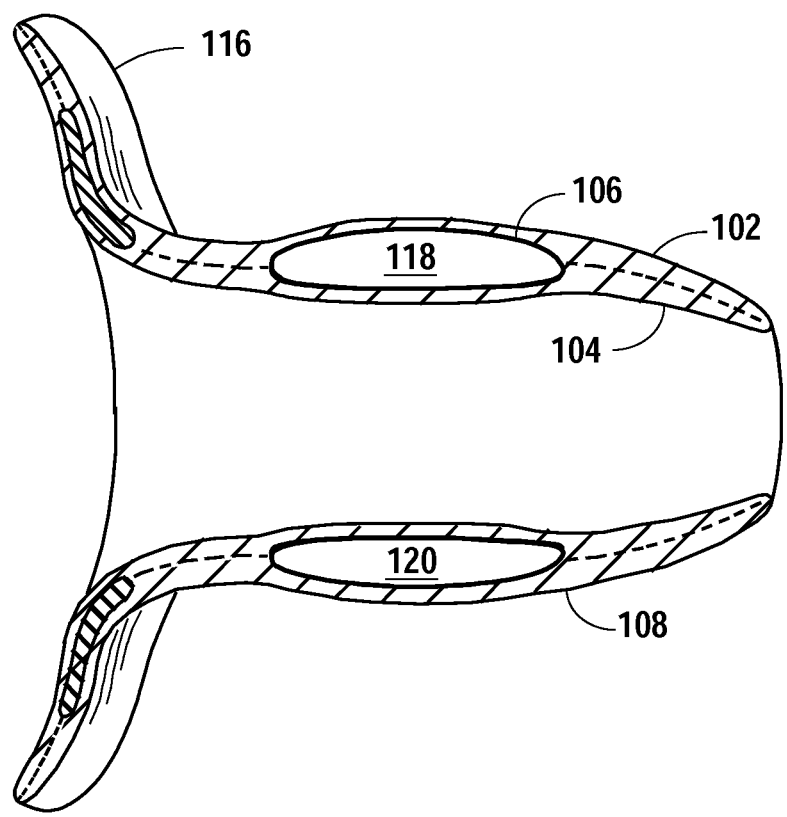
FIG. 1C is a cross-sectional view similar to FIG. 1B wherein the arcuate balloons have been inflated.

The cylindrical portion 114 of penile sleeve 100 has a first flexible non-inflated configuration that facilitates insertion over the penis and a second substantially rigid inflated configuration. In the substantially rigid configuration, the arcuate balloons are inflated (see FIG. 1C) so that chambers 118, 120 expand to stretch cylindrical portion 114 and fiber matrix 130.

Balloons 106, 108 may be inflated simultaneously or independently controlled with respect to each other. The ability to selectively inflate each of balloons 106, 108 enables the cylindrical portion 114 of the penile sleeve to deflect sideways in a controlled manner. In particular, inflation of one of the balloons 106, 108 causes the cylindrical portion 114 to deflect in the opposite direction of whichever of the balloons 106, 108 is inflated. In most cases, balloons 106, 108 will be inflated simultaneously, as will be discussed in more detail below.

A dorsal insert 122 may be interposed between the dorsal folded portions of arcuate balloons 106, 108. Dorsal insert 122 is preferably substantially triangular in cross-section and has an elongated configuration extending along the longitudinal plane of the dorsum of cylindrical portion 114. Dorsal insert 122 may extend into skirt 116 to provide support for cylindrical portion 114. Dorsal insert 122 preferably has a convex wedge-shaped inferior margin which is configured to exert firm but even pressure on the dorsal penile veins as will be detailed hereinafter. Dorsal insert 122 is preferably formed of a firm polymeric material such as silicone.

A ventral insert 124 is disposed on the ventral side of cylindrical portion 114. Ventral insert 124 may be curved so that its concave dorsal portion forms a soft truss underneath a user's urethra. Ventral insert 124 may be formed of a soft polymeric material such as medical grade silicone rubber. Ventral insert 124 is configured to stretch along the circumferential direction upon inflation of arcuate balloons 106, 108 as demonstrated in FIGS. 4A, 4B, 5A, and 5B. This helps avoids undue compression of the urethra and contributes to the circumferential flexibility of penile sleeve 100.

Figure 2A:
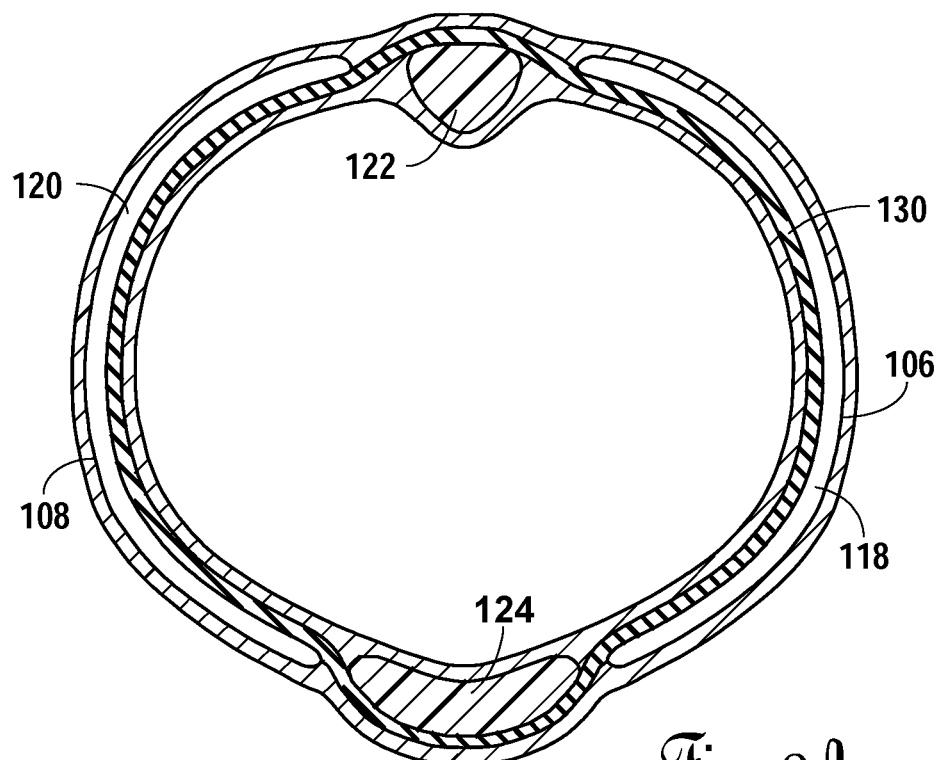
FIG. 2A is a cross-sectional view in the axial plane of the penile sleeve shown in FIG. 1A taken along the line 2A-2A with the arcuate balloons deflated.
Figure 2B:
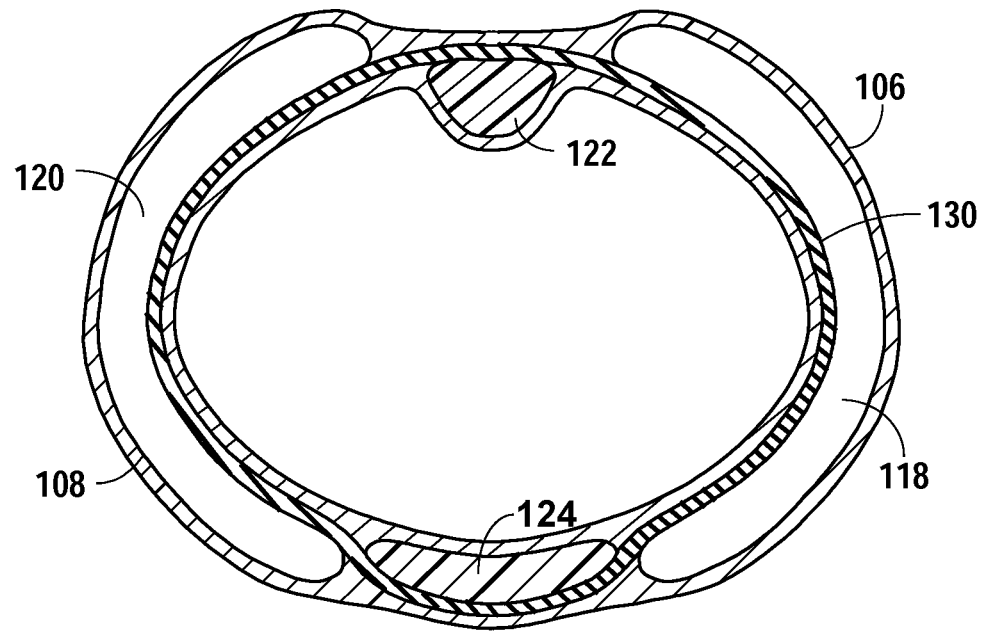
FIG. 2B is a cross-sectional view of the penile sleeve similar to FIG. 2A, following arcuate balloon inflation.

As seen in FIG. 2A, when penile sleeve 100 is in a non-pressurized state, both arcuate chambers 118, 120 are deflated so that the cylindrical portion 114 of penile sleeve 100 is soft and flexible. Arcuate chambers 118, 120 may be partially filled with a non-compressible fluid, such as saline or a free flowing silicone gel. When penile sleeve 100 is in an inflated state (see FIGS. 1C and 2B), cylindrical portion 114 is relatively rigid as a result of pressurized filling of the fiber reinforced arcuate chambers 118, 120, which exert even pressure on the side walls of the erect penile shaft.

Dorsal insert 122 may have a relatively higher modulus of elasticity when compared with the relatively more compliant ventral insert 124. This restricts expansion and reduces the length of penile sleeve 100 upon inflation of the arcuate balloons 106, 108. This results in curvature of penile sleeve 100, which directs the distal aspect of the penile shaft cephalad.

In some embodiments, the curvature of penile sleeve 100 may be controlled by providing offset semi compliant arcuate balloons 106, 108 or having axial or longitudinal segments of variable compliance. In some embodiments, a curve control arrangement comprises a woven or knitted fabric in which the threads extending in the axial versus longitudinal plane have variable compliance and/or weaving pattern thereby inducing differential compliance and curving of penile sleeve 100.

The proximal end of cylindrical portion 114 is coupled to a central portion of radially extending flange or skirt 116, which has a cup-like configuration. The body facing surface 126 of skirt 116 slopes centrally towards a wide aperture 128 which is gently contoured toward the interior of cylindrical portion 114 of penile sleeve 100.

Figure 3A:
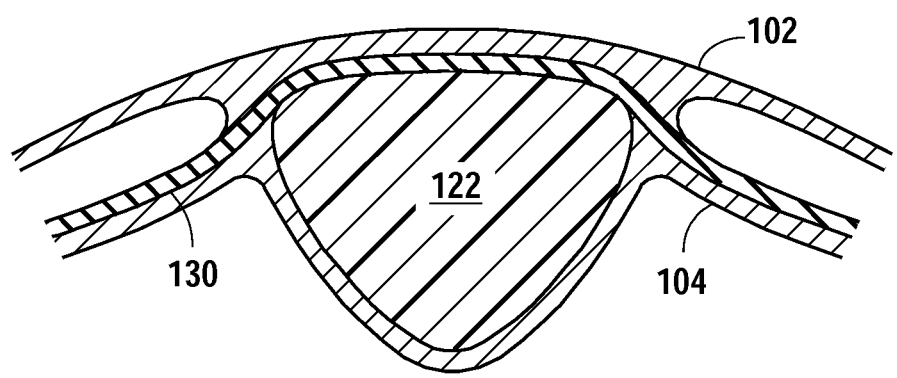
FIG. 3A is a partial sectional view in the axial plane of the dorsal insert shown in FIG. 2A demonstrating the position of the fiber matrix and folded portion of the arcuate balloons to the dorsal insert prior to balloon inflation in one embodiment.
Figure 3B:
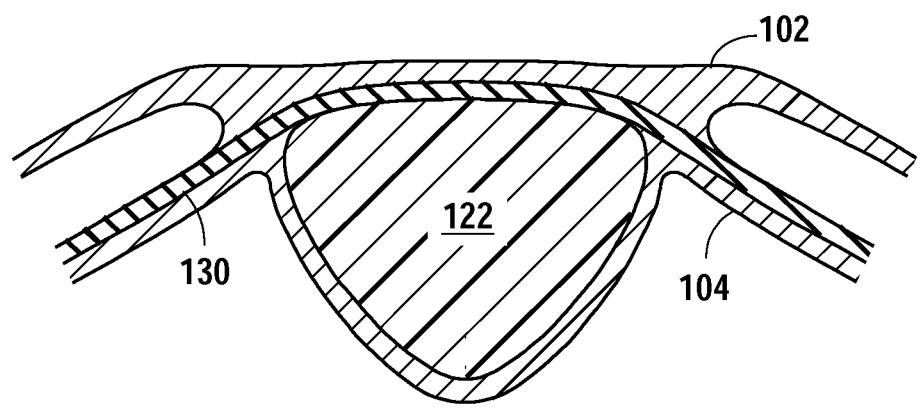
FIG. 3B is a partial sectional view in the axial plane similar to FIG. 3A, demonstrating inward translation of the dorsal insert following arcuate balloon inflation.

FIG. 3A illustrates one embodiment of the position of dorsal insert 122 relative to fiber matrix 130 and folded portions of the arcuate balloons 106, 108 prior to inflation. In the uninflated state, dorsal insert 122 is in a relaxed state as there is no constraining action by the fabric sleeve or arcuate balloons. As illustrated in FIG. 3B, fiber matrix 130 constrains the circumferential expansion of arcuate balloons 106, 108, which creates a force on dorsal insert 122, which translates it inwardly and downwards to compress the dorsal penile veins.

Figure 4A:
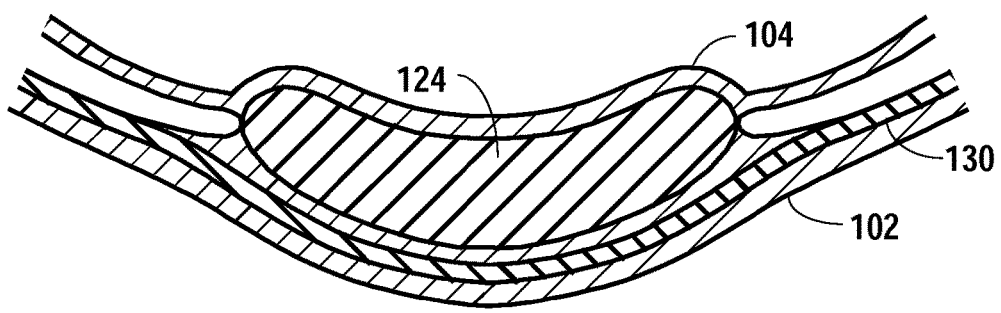
FIG. 4A is a partial sectional view in the axial plane of the ventral insert showing its relationship to the fiber matrix and folded portions of the arcuate balloons prior to arcuate balloon inflation.
Figure 4B:
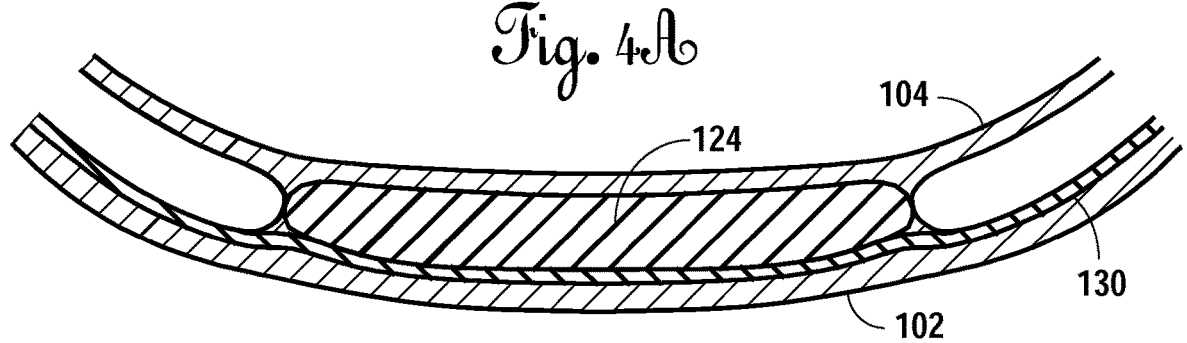
FIG. 4B is a partial sectional view in the axial plane showing the ventral insert and its relationship to the fiber matrix and folded portions of the arcuate balloons, following arcuate balloon inflation, stretching and elongation of the ventral insert and circumferential expansion of the penile sleeve.

Referring to FIGS. 4A and 4B, in an uninflated state, ventral insert 124 is typically curved oval or banana shaped and has a rounded cross-sectional configuration with a concave inner margin 132. Fiber matrix 130 extends along the outer curved wall of the ventral insert 124. The force required to stretch the insert along its circumferential dimension can be tailored to provide appropriate elastic recoil force against the circumferential outward stretching force of the inflated arcuate balloons 106, 108, which is constrained by fiber matrix 130. When inflated, fiber matrix 130 constrains the expansion, causing ventral insert 124 to flatten.

One consideration when selecting an appropriate durometer for the ventral insert is providing adequate cushioning to the underlying urethra and corpus spongiosum. FIGS. 20A, 22A, 22B, 23A, and 23B, illustrate the anatomical relationship of urethra 264 to the surrounding corpus spongiosum 246 which, like corpus cavernosum 244 is made up of erectile tissue. This tissue becomes distended with blood during an erection and is trapped therein as long as the erection is maintained.

Accordingly, ventral insert 124 provides a mechanical and physiologic function in preventing undue compression of the urethra and corpus spongiosum by penile sleeve 100.

Figure 5A:
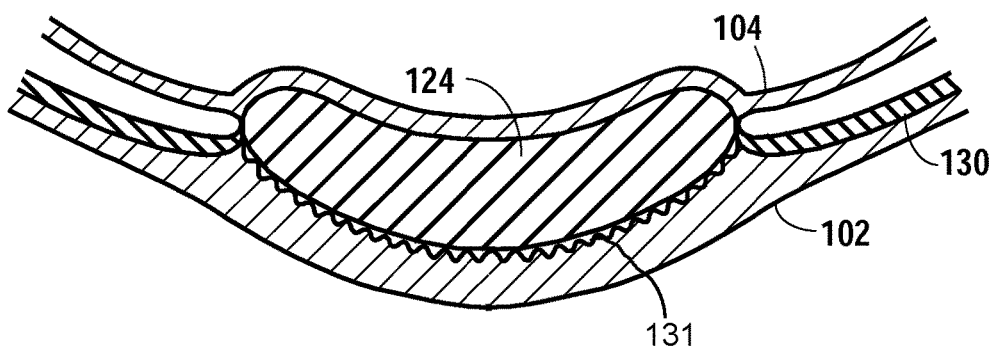
FIG. 5A is a partial sectional view in the axial plane of the ventral insert showing a corrugated fiber matrix coupled to the outer margin of the ventral insert prior to arcuate balloon inflation.
Figure 5B:
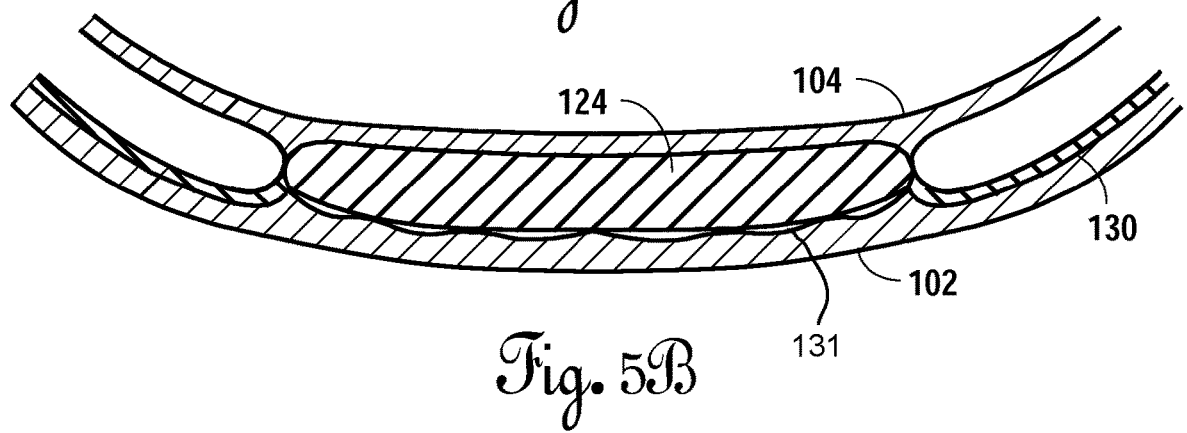
FIG. 5B is a view similar to FIG. 5A following arcuate balloon inflation.

FIGS. 5A and B demonstrate an alternative embodiment of fiber matrix 130 overlying the outer margin of the ventral insert 124. In this particular embodiment, fiber matrix 130 is corrugated 131 in the unstretched state shown in FIG. 5A, and the corrugations flatten and tension upon inflation of arcuate balloons 106, 108 as shown in FIG. 5B.

Figure 6:
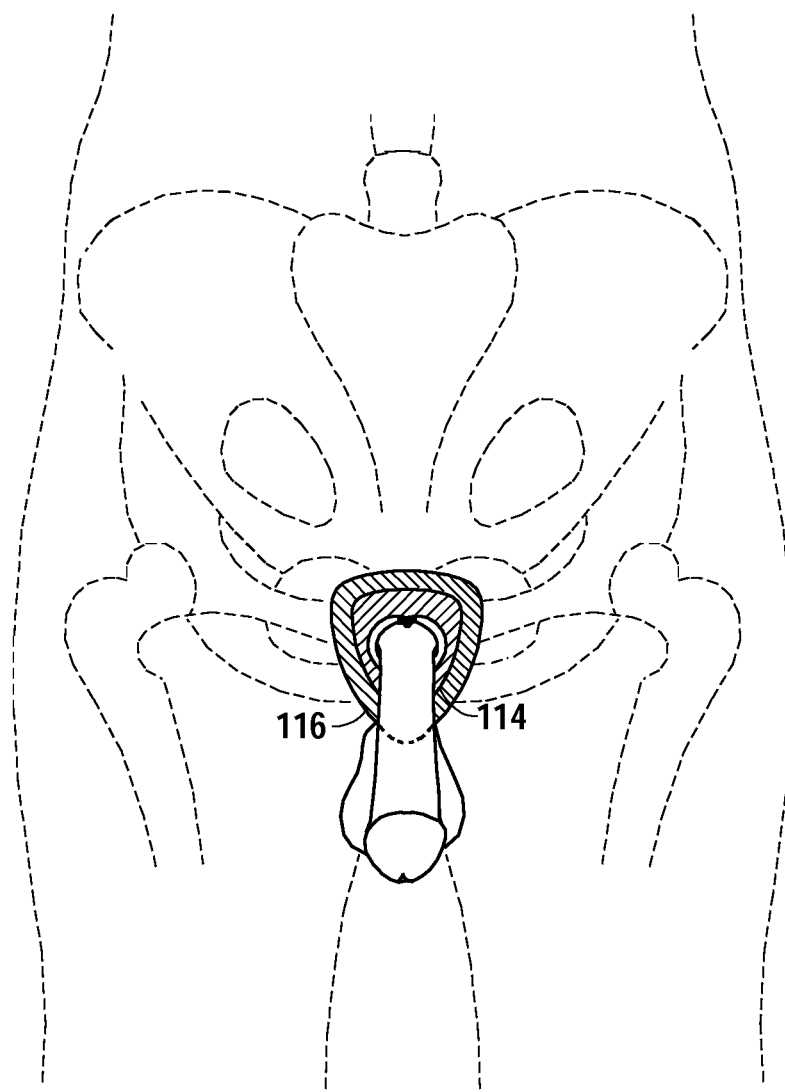
FIG. 6 is a frontal perspective view depicting the trunk of a male user, appearing in phantom outline, with penile sleeve in position over the users groin, showing the cylindrical collar portion superimposed on skirt portion of penile sleeve.

FIG. 6 is a frontal perspective view depicting the trunk of a male user appearing in phantom outline with the penile sleeve 100 in position showing the cylindrical portion 114 on skirt 116 of penile sleeve 100. In this embodiment, skirt 116 has a triangular configuration with rounded sides and angles (Reuleaux triangle) configured to correspond to the general configuration of the users groin.

Figure 7:
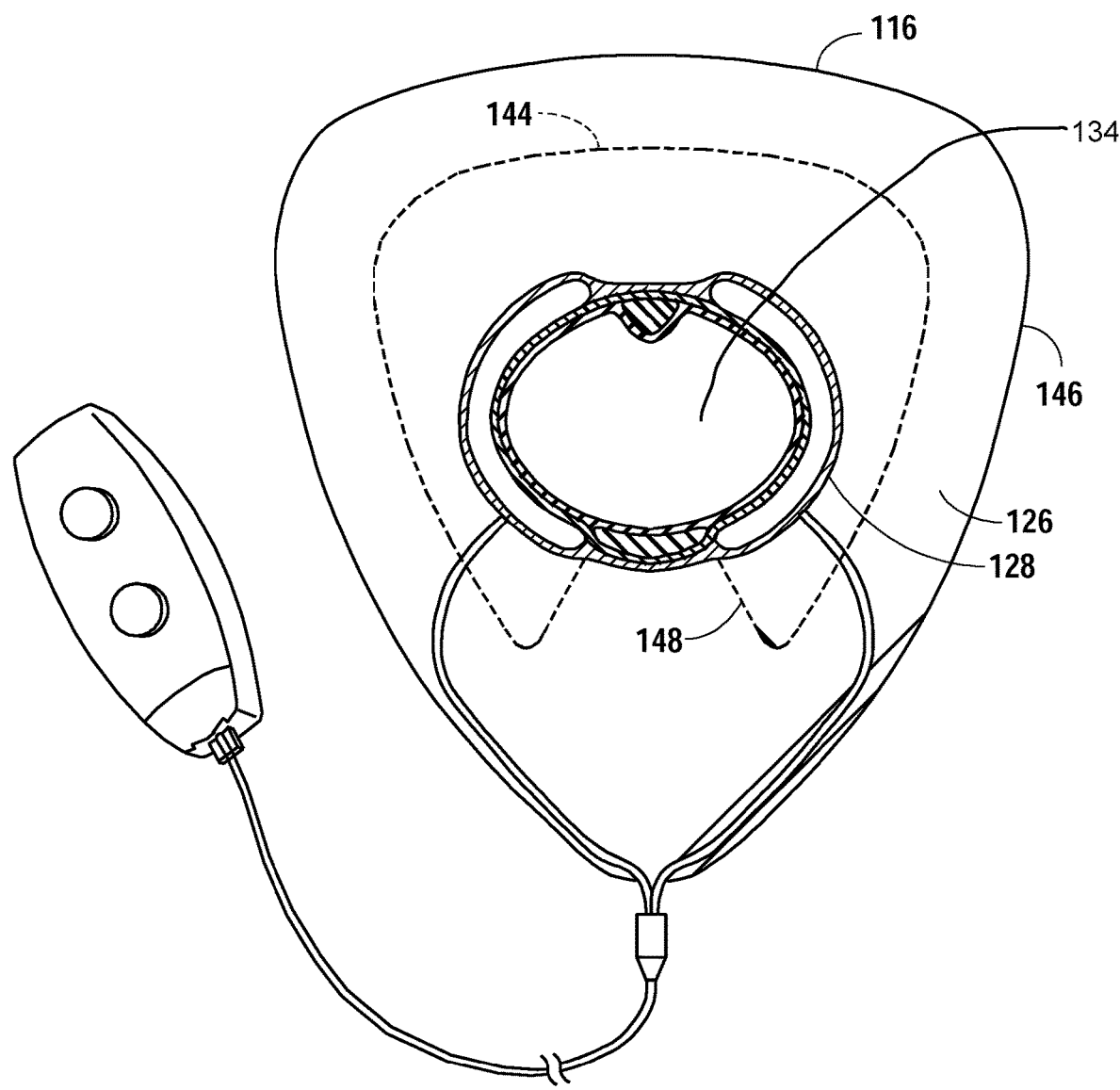
FIG. 7 is an elevational perspective view showing the frontal aspect of skirt 116 portion of the penile sleeve, superimposed thereon.

Referring to FIG. 7, skirt 116 portion of penile sleeve 100 will now be described in more detail. The radially extending skirt portion 116 preferably has a triangular configuration with a proximally, or body, facing surface 126 substantially conforming to a user's groin, and sloping towards a centrally disposed funnel-like aperture 128 leading to the lumen 134 of the cylindrical portion 114. A distally facing surface of skirt 116 is preferably adapted for a soft and comfortable contact with a partner.

As seen in FIG. 7, skirt 116 comprises a relatively firm core element 144 sandwiched between inner and outer layers 102, 104, which extend outwardly to form the soft flange element 146, and distally along the cylindrical portion 114 and the tapered portion.

The ventral aspect of core element 144 is discontinuous, forming a gap 148, in which the outer and inner soft flange element layers are bonded. As noted in FIG. 7, the core element gap 148 corresponds to the position of the ventral insert 124 of the cylindrical collar. The purpose of core element gap 148 is to provide increased flexibility to aperture 128. The minimum diameter of aperture 128 in its relaxed, unexpanded state should be smaller than the diameter of an erect penis with which it is to be used, but large enough and flexible enough to avoid unduly constraining the penis. Although it is believed that most erect adult penises can be accommodated with a single properly sized penile sleeve 100, different sizes can be provided.

Skirt 116 is thickest at the level of aperture 128 and tapers towards the peripheral margin 146. The thickness of skirt 116 is preferably between 3-5 mm.

Skirt 116 may have various tailored configurations to fit snugly against the users groin and to assist in anchoring and stabilizing the rigidized penile sleeve 100, and the erect penis therein against the groin and the underlying pubic bone, thus providing firm dynamic support to the erect penis. The thickness, shape, and flexural compliance of skirt 116 may be varied to provide different characteristics. For example, the various cup-like configurations of skirt 116 portion may provide spring-like elasticity to penile sleeve 100, and to aid in conforming skirt 116 to the users groin.

Core element 144 may be formed integrally with dorsal insert 122. Furthermore, the core element-dorsal insert complex may restrict longitudinal elongation of the dorsal aspect of penile sleeve 100, while allowing unrestrained elongation of the ventral insert; contributing to the differential and directional expandability of penile sleeve 100. This mechanism represents one form of curvature control arrangement. In some embodiments, skirt 116 may have a core of a fiber reinforced insert and outer layers of relatively soft silicone continuous with the rest of the sleeve.

Core element 144 is preferably formed of relatively firm polymer, having an appropriate flexural modulus and a Shore A durometer of about 50-70. Although a material of the described characteristics is preferred, any material which performs satisfactorily and is durable under conditions of use can be employed. Core element 144 and dorsal insert 122 may be formed of the same material and may be molded as a single piece.

Core element 144 and dorsal insert 122 are preferably non-compliant, whereas the ventral insert 124 is compliant. When arcuate balloons 106, 108 are inflated and expanded, and fiber matrix 130 is stretched and under tension, differential and directional expansion forces are created in penile sleeve 100 that cause the penis therein to bend and deflect in a cephalad direction that is oriented away from the more compliant ventral insert. Thus, skirt 116 portion of penile sleeve 100, together with dorsal insert 122, provide a similar function of the penis' own suspensory ligaments, which normally hold the penis base close to the pubic bone and support it when erect.

FIGS. 8A-8G illustrate one embodiment of arcuate balloons 106, 108 and a method of making such a balloon. FIGS. 8A and 8B illustrate a tubular elastomeric precursor 160 of an arcuate balloon. Precursor 160 has a tubular wall 162 defining the boundary between the interior and exterior of precursor 160. The interior 176 extends longitudinally between a proximal end 164 and a distal end 166.

Referring to FIG. 8G, proximal end 164 of tubular elastomeric precursor 160 has been coupled to an inflation tube 168 at inflation port 170 to provide fluid access to interior 176. Distal end 166 has been sealed by approximating and bonding together an inner curved wall portion and an outer curved wall of the tubular elastomeric precursor 160.

FIGS. 8C-8F illustrate an arcuate balloon 106, 108 following the application of negative pressure by inflation tube 168. The inner and outer walls 172, 174 have formed an interior chamber 176 with an arcuate configuration. FIGS. 8D and 8E show stages of further balloon deflation and further approximation of the curvature wall portions. FIG. 8F shows apposition of the balloon walls, and a distal end of the balloon wall has been sealed, creating arcuate balloon interior chamber 176.

The arcuate balloons may be formed of a variety of elastomeric materials well known in the art including silicone, nylon, PEBAX, or any thermoplastic material. Multilayered balloons may be comprised of multiple layers of the same material, or layers of different materials.

The arcuate balloons may be formed using co-extrusion techniques and then placed into a specialized mold, and radially expanded into an arcuate configuration, and heat set at a suitable temperature. The ultimate burst strength of such balloon is not critical as the pressure needed for this application is relatively low when compared to balloons utilized for other medical purposes, such as angioplasty and kyphoplasty.

An arcuate balloon may be formed from polymeric tubular preforms which may be formed using any suitable method known in the art. In some embodiments, the method suitably includes forming a tubular portion, stretching the tubular portion, placing the tubular portion in a balloon mold, and forming a tubular balloon by radially expanding the tubular portion into the balloon mold. The balloon is then heat set. The heat set process may be performed in a specialized mold that converts the cylindrical tubular balloon into an arcuate configuration. Other methods of balloon forming with stretching and radial expansion are disclosed in U.S. Pat. Nos. 5,643,279, 5,913,861, and 6,946,092, each of which is incorporated herein in its entirety.

The inner and outer curved walls 172, 174 may comprise various materials. For example, the outer curved wall 174 may be comprised of a material different from the inner curved wall 172. Further, the outer curved wall 174 may be of the same or different thickness, compliance, fiber reinforcement, burst strength, etc. Care is taken to maintain flexibility of the arcuate balloons 106, 108 as the balloon layers may be kept separate to avoid problems of compliance mismatch between fiber matrix 130 and the balloon layer or layers.

In some embodiments, the arcuate balloons may be offset and have axial or longitudinal segments of variable compliance to control curvature.

In some embodiments, arcuate balloons 106, 108 may be constrained within fiber matrix 130, as will be discussed in more detail below. In other embodiments, arcuate balloons 106, 108 may unconstrained to maintain the overall flexibility of penile sleeve 100. In other embodiments, only one wall portion of the arcuate balloon is constrained to impart certain mechanical properties such as a focal constraining action. Fiber matrix 130 may form one layer in a multilayered balloon. In other embodiments, fiber matrix 130 is separate such that the layers are allowed to slide with respect to each other.

In one embodiment, an arcuate balloon is semi-compliant and may be inflated and deflated, and when inflated exhibits a moderate change in distention due to its arcuate configuration, which tends to keep the intraluminal inflation pressure low. In other words, the walls of the arcuate balloon exhibit inward and outward displacement rather than stretching when subjected to inflation pressures appropriate for this application. At such low pressures, fiber matrix 130, as well as the inherent elasticity of the soft silicone, constrains the arcuate balloons to minimize over-inflation.

In one embodiment, the arcuate balloons are compliant and are formed of silicone by a dispersion dipping process, injection molding, or other manufacturing techniques known in the art.

The arcuate configuration of the balloons enables the balloons to be folded into a small circumferential configuration to keep the deflated wall thickness of penile sleeve 100 as thin and as flexible as possible. Furthermore, the use of independent or separate multilayered constructs may streamline the manufacturing process, while providing more design versatility, efficiency, and miniaturization.

The arcuate balloons may be produced by extruding thermoplastic polyimide tubing and then expanding the extruded tubing axially and radially within a specialized mold. Thin wall balloons of high strength may be formed by this process of blow molding known in the art. This technique is discussed in U.S. Pat. No. 4,490,421 for forming PET balloons. The expandable balloons may also be made of a PEBA material such as PEBAX.

Generally, fiber matrix 130 of penile sleeve 100 is designed to balance properties such as stretchability/flexibility when in a relaxed state to facilitate application of penile sleeve 100; compliance versus resistance to circumferential and/or longitudinal expansion; and flexural resilience versus spring-like support to the base of the penis when expanded.

Referring to FIGS. 10A-10G, fiber matrix 130 may be omitted or placed in different configurations. In the embodiment shown in FIG. 10A, the cylindrical portion 114 of penile sleeve 100 comprises an inner and outer silicone layers 102, 106, arcuate balloons 106, 108, dorsal insert 122, and ventral insert 124. In this configuration, a fiber matrix is omitted. The arcuate balloons 102, 106 and inserts 122, 124 may be integrally molded with the silicone layers in such a way that pressurized inflation of the paired balloons creates an outward circumferential expansion of the sleeve that causes the dorsal insert to translate inward to achieve focal compression of the dorsal penile veins, and stretching of the compliant ventral insert that increases the sleeve circumference and protects the urethra.

Figure 10A:
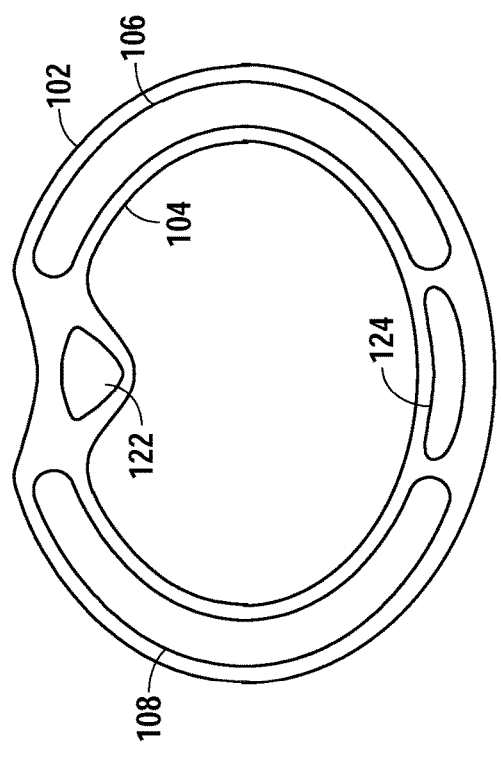
FIG. 10A is a cross-sectional view taken in the axial plane along the line 10A-10A of a penile sleeve showing the sleeve components without a fiber matrix.
Figure 10C:
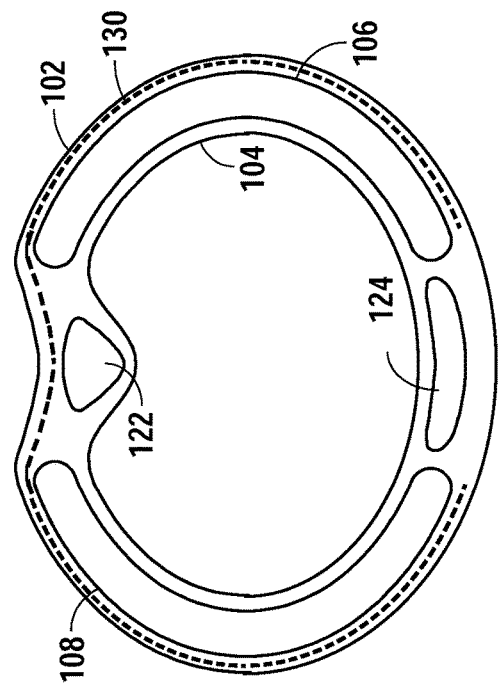
Figure 10B:
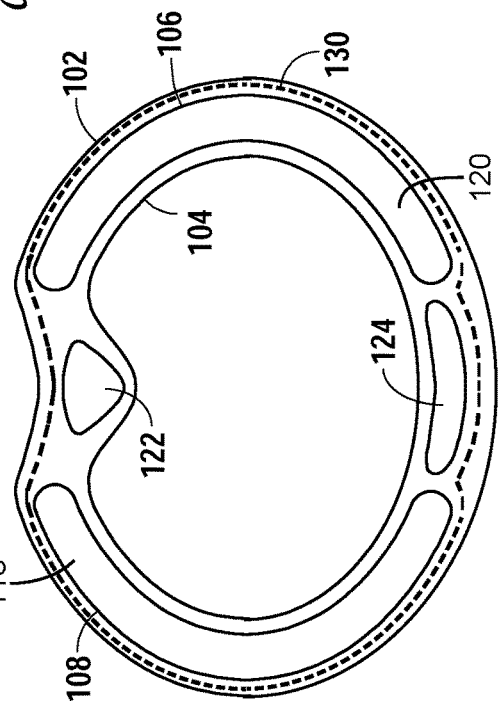

In the embodiment shown in FIG. 10B, a fiber matrix is present circumferentially in the intermediate layer. The enclosed pair of arcuate chambers 118, 120 are configured to expand in response to an increase in pressure within the chambers. Fiber matrix 130 constrains the expansion of the chambers 118, 120; however, the fabric sleeve may be semi-compliant, allowing some elasticity to penile sleeve 100. The arcuate balloons 106, 108, inserts 122, 124, and fiber matrix 130 are encapsulated within the elastic silicone shell 102, 104.

In the embodiment shown in FIG. 10C, fiber matrix 130 of penile sleeve 100 extends only partially within the intermediate layer, around the outer curved wall of arcuate balloons 106, 108, and over dorsal insert 122, but does not extend over ventral insert 124. This allows for penile sleeve 100 circumferential compliance and avoids compression of the urethra.

In the embodiment shown in FIG. 10D, individual tubular fiber matrices 130A, 130B are utilized to encase arcuate balloons 106, 108, which may be in the form of conventional textile fabrics, ePTFE, or other fiber coatings. A pair of individual composite structures are formed that include the polymeric balloons, and textile substrates in an integrated polymeric casing. The casing is preferably silicone. However, other polymers for use in making the casing include, but are not limited to urethanes, polyesters, or ePTFE.

In the embodiment shown in FIG. 10E, fiber matrix 130 covers only the inner curved wall portions of arcuate balloons 106, 108.

In the embodiment shown in FIG. 10F, fiber matrix 130 covers only the outer curved wall of arcuate balloons 106, 108.

Fiber matrix 130 may be formed with one single continuous fiber arranged both longitudinally and orthogonally, or, the matrix may be formed using multiple fibers. In such embodiments, the longitudinal fibers as well as the orthogonal fibers may be formed by the same or different strands of fiber or a combination thereof. In reference to FIGS. 12A-12F, fiber matrix 130 may comprise one or more longitudinal fibers 180 and one or more generally orthogonal fibers 182. The term "longitudinal fibers" refers to fibers that extend between the proximal and distal ends of penile sleeve 100. The term "orthogonal fibers" refers to fibers that cross the longitudinal fibers at various angles.

Figure 11B:
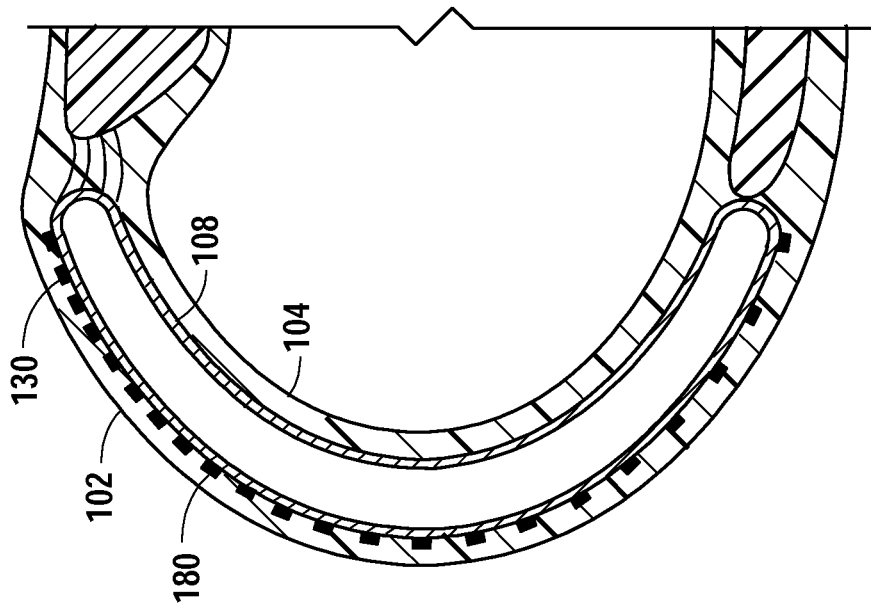
FIG. 11B is a view similar to FIG. 11A showing an alternative fiber density whereby the fiber density decreases progressively from dorsal to ventral.
Figure 11A:
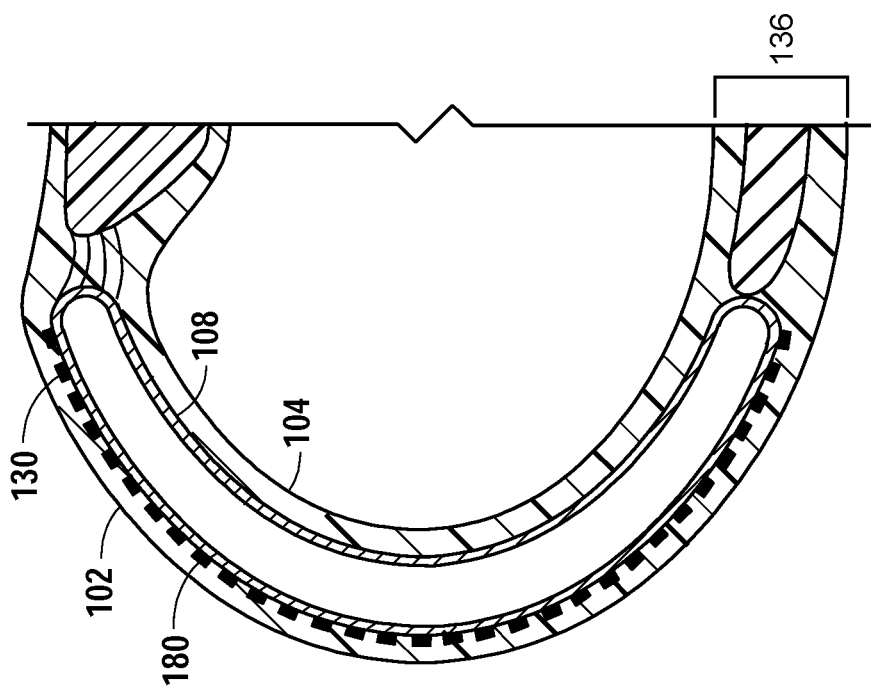
FIG. 11A is a cut away partial cross-sectional view of penile sleeve showing the relationship of a fiber matrix to the arcuate balloon illustrated in FIG. 10F, whereby fiber density is uniform.

FIGS. 11A and 11B are cut away, enlarged, partial cross-sectional axial sections of wall 136 of penile sleeve 100, further illustrating construction of arcuate balloon 102. As illustrated, longitudinal fibers 180 are ribbon shaped to reduce the thickness of the wall 136. In this particular embodiment, longitudinal fibers 180 are applied to the outer curved wall only. In other embodiments, both the outer and inner curved wall portions may include longitudinal and/or axial fibers.

Figure 12A:
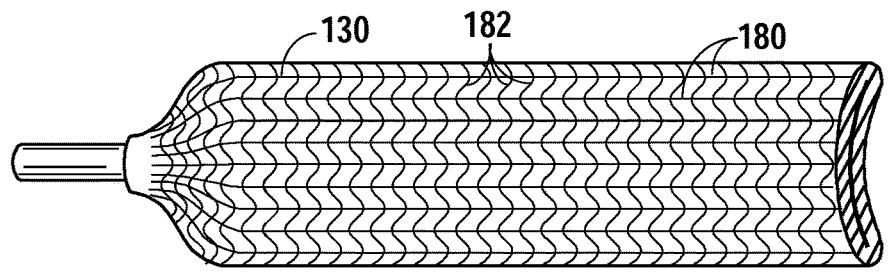
FIG. 12A is a schematic perspective view in the longitudinal plane of an arcuate balloon similar to FIG. 8G following application of a fiber matrix.
Figure 12B:
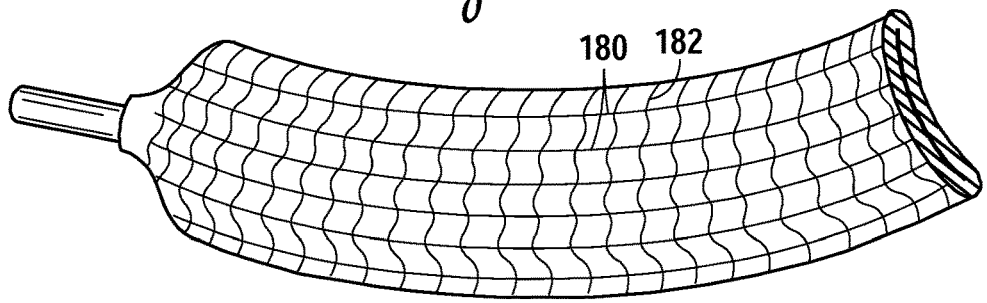
FIG. 12B is a view similar to 12A with a different fiber configuration.

Turning to FIG. 11B, in one embodiment, the longitudinally oriented fibers 180 at the dorsal aspect of penile sleeve 100, have a fiber density of generally 20-30 fibers/inch, and a fiber thickness of about 0.0005-0.025 inch, and are placed relatively close to each other. In this embodiment, the fiber density decreases progressively from dorsal to ventral. In other embodiments, the fiber compliance or elasticity increases from dorsal to ventral. The net effect of either decreasing fiber density or increasing fiber elasticity towards the ventral aspect of penile sleeve 100, is relatively increased differential expansion of the ventral aspect of the sleeve upon balloon inflation. This leads to longitudinal curving of penile sleeve 100 as illustrated in FIGS. 12A-12B, and represents another form of curvature control arrangement Fiber matrix 130 is preferably made of a woven or knit fabric which provides a limited predetermined degree of compliance to allow appropriate circumferential stretching of the device around the penis during placement and during engorgement of the corpora cavernosa and erection. One exemplary form of woven fabric is shown in FIG. 12A. As seen in the drawing, the orthogonal threads 182 along the circumferential plane (axial plane) of penile sleeve 100 device are generally sinusoidal and the longitudinal extending threads 180 of the fabric are generally straight. Fiber matrix 130 and the adjacent silicone casing are preferably bonded. During manufacturing, fiber matrix 130 is placed around the arcuate balloons and is coated with a liquid silicone coating to form a silicone coated fabric encasing the balloon layers.

Inflatable penile sleeve 100 construction may be integral or unitary in which the balloon layer, fabric layer, and silicone casing are manufactured as a single unit, alternatively the construction may be comprised of providing separate balloons to which fabric layers and silicone casing are incorporated by injection molding, dip molding, adhesive or other bonding.

An alternative curve control arrangement comprises a woven or knitted fabric in which the orthogonal and longitudinal threads have variable compliance and/or weaving pattern thereby inducing differential compliance and curving of penile sleeve 100.

In the embodiment shown in FIGS. 11A and 11B, longitudinal fibers 180 are applied to the outer curved wall only. As discussed with respect to FIGS. 10A-10G, other configurations are possible.

Referring to FIG. 12A, there is shown an arcuate balloon having a thin wall and high burst strength having a fiber matrix formed as a tubular sleeve. The braided fiber sleeve surrounds at least a portion of the base balloon, wherein the greater and lesser curvature portions of the arcuate balloon are fiber reinforced.

In one configuration, a semi-compliant arcuate medical balloon may include a fabric sleeve formed as a separate free standing article that is subsequently pulled over the base arcuate balloon. Alternatively, the fiber sleeve may be pulled over a tubular preform and subsequently processed together and heat set to form a fiber reinforced arcuate balloon.

In another configuration, the fabric sleeve may be formed in-situ over the base arcuate balloon. In one variation, fiber matrix 130 is formed from substantially semi-elastic ribbon-shaped fibers, each having a width greater than thickness.

Referring again to FIG. 12A, in one aspect the fiber reinforced arcuate balloon is braided from at least three substantially inelastic fibers intertwined so that no two of the three fibers are twisted exclusively around one another. The fibers may be secured to the base balloon with an adhesive or, alternatively, fused to the base balloon.

In the configuration shown in FIG. 12A, the longitudinal fibers are relatively straight and the radial or circumferential are curved and generally sinusoidal. When in a relaxed state, the circumferential fibers provide penile sleeve 100 with the required degree of flexibility and stretchability required for ease of use. When expanded, the sinusoidal fibers all circumferential expansion of the sleeve 10, whereas the straight longitudinal fibers provide flexural rigidity to the sleeve that is required to maintain a penis in an erect state.

Figure 12C:
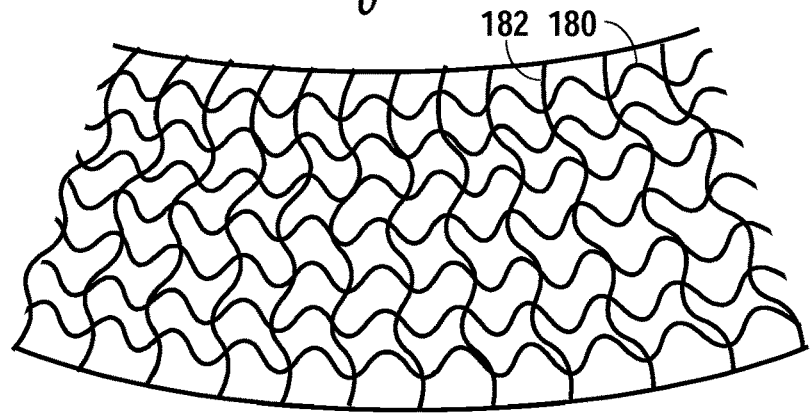
FIG. 12C is an enlarged cut away partial cross-sectional view showing sinusoidal fiber placement in the longitudinal and orthogonal planes.
Figure 12D:
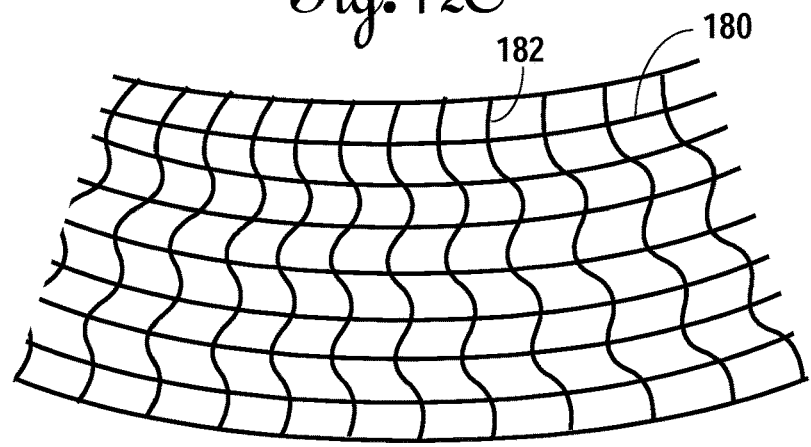
FIG. 12D is an enlarged cut away cross-sectional view similar to FIG. 12C whereby longitudinal stretching of fiber matrix has resulted in straightening of the longitudinal fibers whereas the orthogonal fibers remain sinusoidal.

FIG. 12B illustrates another curvature control arrangement whereby the radial fibers are arranged to provide a higher fiber density along the dorsal aspect of the arcuate balloon, with the fibers along the ventral aspect being more widely spaced. When the arcuate balloon is inflated, there is differential expansion along the ventral aspect causing penile sleeve 100 to bend accordingly. FIGS. 12C and 12D provide alternative sinusoidal fiber architectural patterns that can be tailored for particular differential expansion/restriction purposes.

Figure 12E:
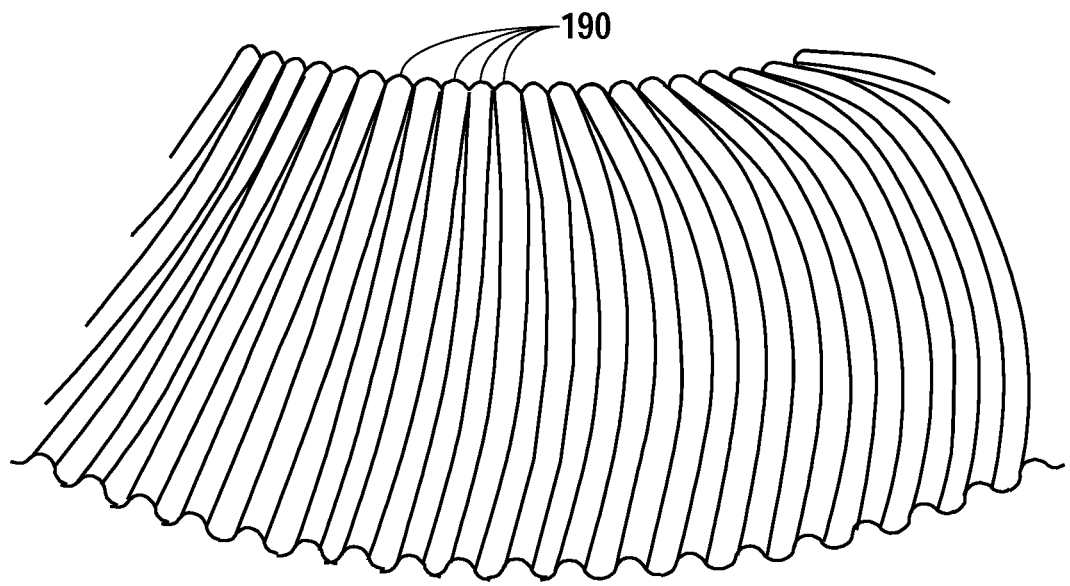
FIG. 12E is a schematic frontal perspective of one embodiment of a fiber matrix for an arcuate balloon utilizing stitching or sectional crimping of a number of fiber folds along the dorsal aspect of the arcuate balloon to cause expansion restriction and curvature of the arcuate balloon.
Figure 12F:
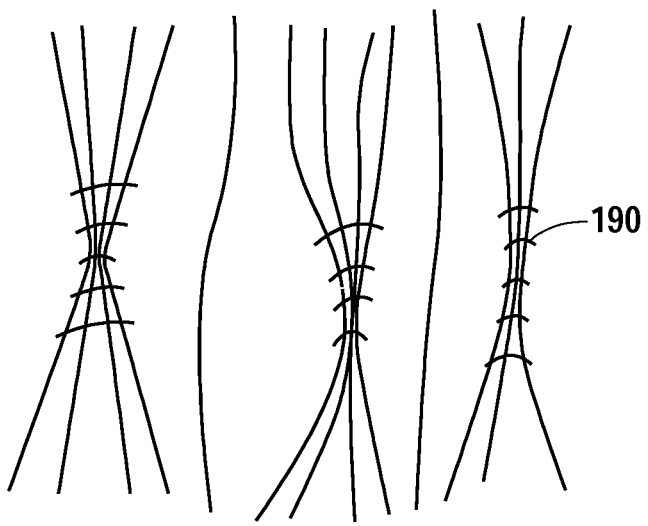
FIG. 12F is a detailed view demonstrating stitching of ridges along a longitudinal axis of the fiber matrix of FIG. 12E.

As demonstrated in FIGS. 12E and 12F, restriction of the expansion of the dorsal aspect of penile sleeve 100 may be done by stitching or sectional crimping a number of folds or corrugations 190 in the fiber matrix, whereby upon circumferential expansion of the sleeve, following arcuate balloon inflation, the diametrically opposed ventral side can extend more than the dorsal side, thereby forming a curve in penile sleeve 100.

Figure 13:
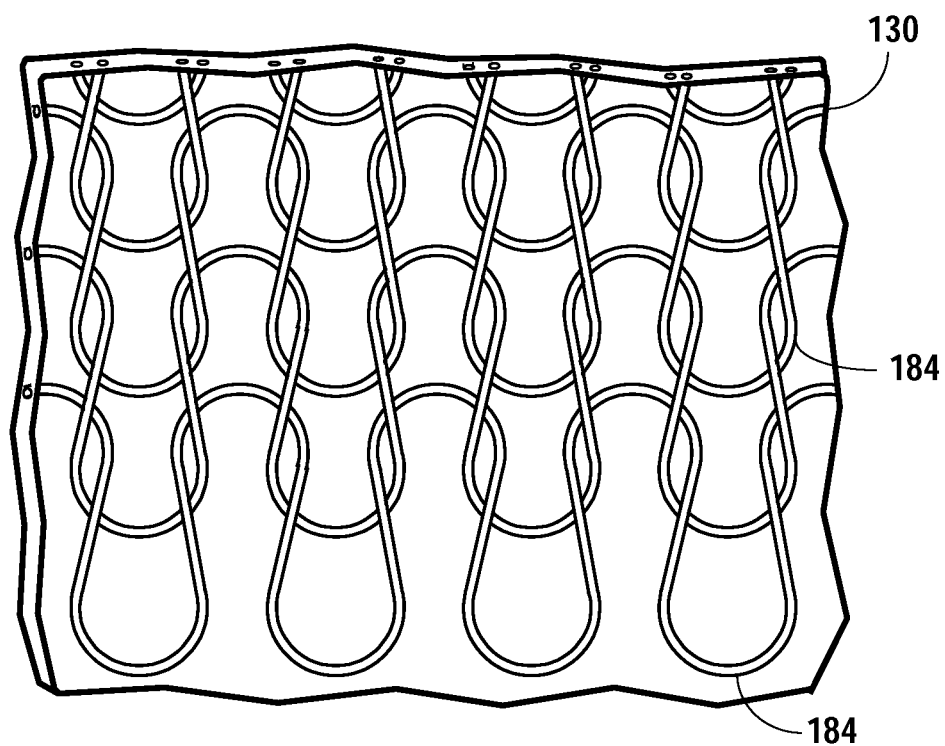
FIG. 13 is an enlarged partial cross-sectional view of an arcuate balloon having a knitted fiber matrix in accordance with one embodiment of the disclosure.

FIG. 13 provides a knitting configuration that may be used as a fiber matrix 130 for penile sleeve 100. The knitting configuration is produced by intertwining threads in a series of interconnected loops 184 rather than by weaving. In this fashion, the loops are mechanically interlocked. A weftknitted structure consists of horizontal, parallel courses of fibers, and requires only a single fiber. Alternatively, warp knitting or circular knitting structures may be produced.

As illustrated in FIG. 13, the knitted fiber reinforcement has a large amount of open spaces between the fibers. Unlike other medical applications where graft porosity is an issue, for the purpose of this application, loose fiber architecture is considered a major advantage as far as flexibility and stretchability when incorporated into a penile sleeve 100 design.

Figure 14:
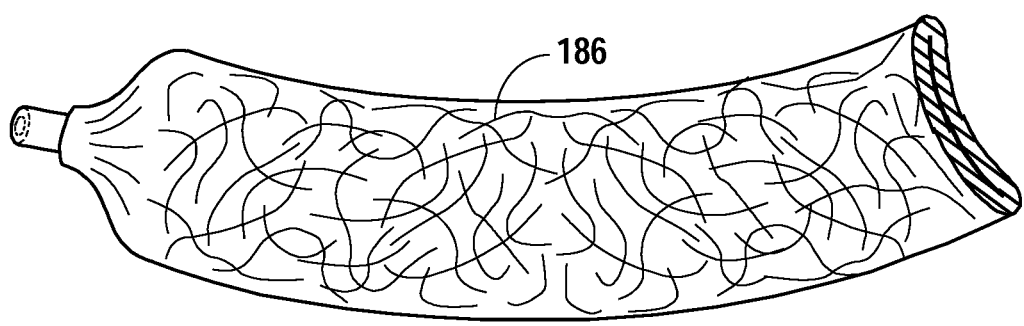
FIG. 14 is a frontal view of an arcuate balloon coated with randomly disposed fibers.

FIG. 14 illustrates an alternative embodiment for providing fiber reinforcement to a penile sleeve 100. The arcuate balloons 102, 106 of penile sleeve 100 may be provided with one or more layers of rotational spun fiber coating 186. Multilayer construction may be used to impart a wide variety of design features including diminished wall thickness, increased strength, flexibility, differential restriction, and curvature control features.

Penile sleeve 100 is preferably made of a liquid elastomer such as silicone supplied by NuSil Technology of Carpenteria, Calif. The product is described as a two part system which is platinum cured. The pre-mixed liquid parts A and B are injected into a preheated mold which is then heated further to 275-320 degrees F. Curing time ranges between 5-10 minutes. A wide range of products of various durometer and other characteristics are available.

Referring now to FIGS. 15A, 15B, 15C, 15D, and 16A, 16B, and 16C, an embodiment of penile sleeve 100 is illustrated. Sagittal cross-sectional view 15A demonstrates inner and outer soft silicone layers 102, 104 (separated by a dotted line which represents a layer of bonding material) between the two layers.

FIGS. 15B, 15C, 15D and FIGS. 16B and 16C illustrate disassembled components, viewed sectionally, including inner silicone layer 104, outer silicone layer 102, dorsal insert 122, which is continuous with the firm core element layer 144 of skirt 116, and ventral insert 124. The different components may be injection molded separately, according to techniques well known in the art.

FIG. 16A is a cross-sectional view in the axial plane of penile sleeve 100 of FIG. 15A taken at the line 16A-16A. FIGS. 15C and 16B are disassembled outer silicone layer 104, and FIGS. 15C and 16C are inner silicone layer 102, which may be injection molded separately as mentioned above. FIG. 16A shows arcuate balloons 106, 108 within an intermediate space between inner silicone layer 104 and outer silicone layer 102. The position of dorsal and ventral inserts 122, 124 are shown in dotted outline in FIGS. 16B and 16C.

With further reference to the inner and outer silicone components shown in FIGS. 15B, 15C, 15D, 16B, and 16C, the molded components of penile sleeve 100 may be removed from the mold and further vulcanized for 20-45 minutes in a separate oven at 275-375 degrees F. Penile sleeve 100 may then be assembled as a composite soft-tissue prosthesis. A mandrel (not shown) is provided having an outside diameter and configuration as the inner margin of the inner silicone layer shown in FIGS. 15B and 16C. The mandrel preferably has a smooth outer surface and may be formed of metal or polymer. The inner silicone layer 102 is placed over the mandrel; dorsal and ventral inserts 122, 124 are positioned in the corresponding grooves 152, 154 along the outer margin of the inner silicone layer 102, and are temporarily bonded by a suitable adhesive, preferably a silicone adhesive. Fiber reinforced arcuate balloons 106, 108 are positioned over the outer margin of the inner silicone layer 102 and glued temporarily in place, and the outer silicone layer 104 is positioned over the entire assembly. A two-part outer mold is placed over the components and the entire assembly is compressed and placed into an oven at a sufficiently high temperature to bond the layers together. The arcuate balloons and fiber matrix 130 may be bonded together earlier as a separate step. Generally, the heat-conditioning should not interfere with the resiliency and/or elasticity of penile sleeve 100, although it may shrink slightly. The heat-conditioning parameters are chosen based upon the properties of the synthetic materials being used to form the fabric sleeve, arcuate balloons, inserts, and silicone layers. Typically, heat-conditioning is carried out at a temperature range from about 100 degrees C. to 220 degrees C. using a convection oven for a time of about 20 minutes. Other means of using the components may also be used.

Referring now to FIG. 7 which illustrates skirt 116 portion of penile sleeve 100, the inner and outer silicone layers 102, 104 flange out at skirt 116 portion, and are bonded together at the peripheral aspect of skirt 116. Centrally, firm core element 144 is sandwiched between the two layers. As mentioned previously, core element 144 is integral with dorsal insert 122.

In one embodiment, the manufacturing process of forming the different components of the cylindrical portion 114 include skirt 116 portion in the above described mold-in steps described above. Furthermore, the flexible tubing 178 within the wall of skirt 116 providing fluid for the paired arcuate balloons 106, 108 are molded-in between inner and outer layers 102, 104, within tubular grooves (not shown) formed between the layers to produce a seamless skirt portion.

An alternative method of making the composite penile sleeve 100 includes dip-casting the inner silicone layer with dorsal insert 122, ventral insert 124, and arcuate balloons 106, 108, positioned thereon onto a silicone dispersion or a polyurethane resin to form the outer layer, thus encasing the intermediate layer components. The composite structure is preferably heat-conditioned to bond the layers together in a final step.

In order for fiber matrix 130 and arcuate balloons 106, 108 to meltably fuse or securely bond together, fiber matrix 130 may be formed of fibers which are similar in melting temperature and bonding capability to that of the inner and outer layers. For example, fiber matrix 130 may be made from fibers such as PTFE, ethylene chlorotetrafluoroethylene, FEB, or polyvinyl fluoride.

The methods for making external penile sleeve 100 described herein are merely illustrative of several methods of manufacturing polymeric composite prostheses. It will be obvious to those skilled in the art that alternative methods of making a penile sleeve 100 may be used without departing from the scope or spirit of this invention. For example, a specialized mold may be provided that comprises an enclosure where the separate components of penile sleeve 100 are thermally processed together at high pressure and/or appropriate temperature. This step may be followed by a separate injection molding or dip molding of the outer soft silicone layer to form the inflatable penile sleeve 100.

Figure 17:
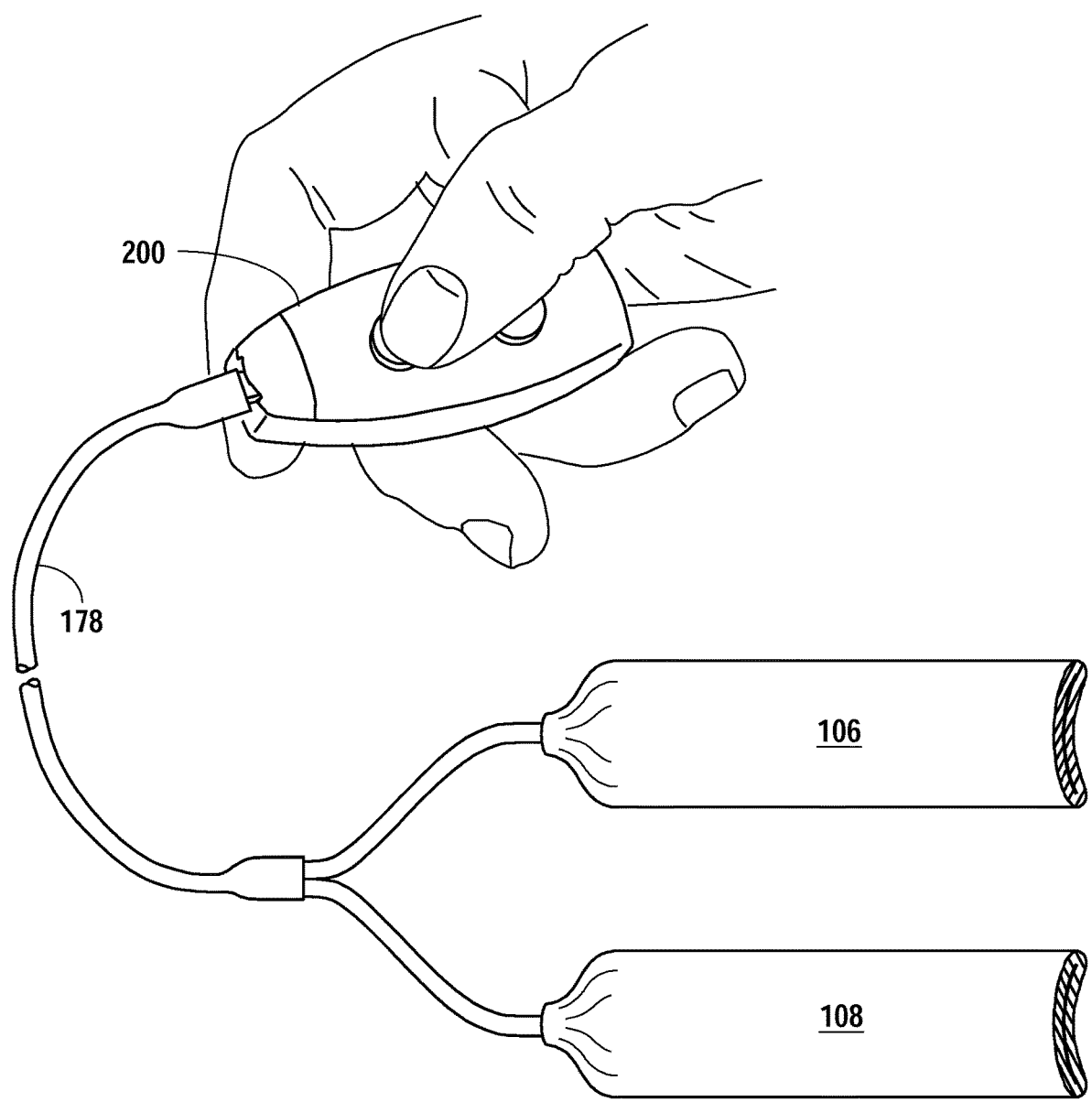
FIG. 17 is a perspective view showing components of the fluid transfer apparatus of the present disclosure.

Referring to FIG. 17, a fluid transfer apparatus 200 for penile sleeve 100 is connected by flexible tubing 178 to the pair of arcuate balloons 106, 108 of penile sleeve 100. Hydraulic fluid present in a reservoir within fluid transfer apparatus 200 can be transferred through the flexible tubing to the arcuate chambers of penile sleeve 100 to pressurize them and to make the sleeve expanded and rigid.

Any pump suitable for external medical operations, such as an inexpensive miniature finger operated fluidic pump, may be utilized. It will be appreciated by those skilled in the art that a variety of pump mechanisms other than those disclosed can be used with the present device, including pumps similar to those shown in U.S. Pat. Nos. 3,458,090 and 7,819,291. Referring to FIG. 18, one suitable fluid transfer apparatus 200 includes an inflatable fluid reservoir 202, a pumping element 204, a flap valve 206, a check valve 208, and a pressure control valve 210; all compactly enclosed within a unit housing 212. The pumping chamber 214 can be operated manually by repetitive pressing of pump button 216, transferring pressurized fluid from distensible reservoir 202 through tubing 178 to arcuate chambers 106, 108.

Pressure control valve 210 can be operated manually by pressing the control button 218 conveniently located next to pump button 216 on the surface of inflation-deflation unit 200. Pressure control valve 210 will also open automatically when a predetermined hydraulic pressure is exceeded in the arcuate balloons 106, 108. When penile sleeve 100 is in a non-pressurized state both arcuate balloons 106, 108 are partially filled with a non-compressible hydraulic fluid, which may be a sterile fluid such as water, saline, or a free flowing silicone gel. Arcuate balloons 106, 108 are coupled to inflation-deflation 200 unit via flexible tubing 178 at unit outlet 226.

The pumping chamber 214 for pressurizing the arcuate balloons 106, 108 and the pressure control valve 210 for limiting increased fluid pressure in the inner chambers will now be described. As seen in FIG. 18, there is a passage which leads from reservoir 202 to pumping chamber 214 of pump 204. The exit passage 228 is closed by one-way flap valve 206, which closes when fluid pressure in pumping chamber 214 exceeds that in reservoir 202. Between reservoir 202 and flap valve 206, there is a T connection 220 to bypass conduit 222, which returns fluid from pressure control valve 210. A pump shaft 224 can be manually pressed into housing 212 against a spring force (not shown) by the user pressing pump button 216 attached to pump shaft 224.

At the outlet of pumping chamber 214 is a passage 230 with an outlet check valve 208. Check valve 208 is normally kept seated, closing passage 230 by fluid pressure in the arcuate balloons 106, 108. However, when pumping chamber 214 is pressurized by depressing pump button 216, and the fluid pressure in pumping chamber 214 and passage 230 exceeds that in arcuate balloons 106, 108, fluid is allowed to flow through check valve 208 towards arcuate balloons 106, 108, as indicated by the arrows.

Penile sleeve 100 is pressurized by sequentially depressing pump button 216 to force hydraulic pressure from pumping chamber 214 into arcuate balloons 106, 108 under pressure. Thereafter, when outlet check valve 208 closes, a reduced pressure is formed in pumping chamber 214 and as a result, flap valve 206 opens, allowing fluid to flow from reservoir 202 into pumping chamber 214. Whenever the pressure in pumping chamber 214 equals or exceeds that in reservoir chamber 202, flap valve 206 closes passage 228. When arcuate balloons 106, 108 are sufficiently inflated and penile sleeve 100 is sufficiently pressurized and rigid, the pumping is stopped whereby the passage 230 is closed by pressure of the fluid in arcuate balloons 106, 108 acting on check valve 208. As a result, arcuate balloons 106, 108 remain filled, pressurized and rigid until the pressure control valve 210 is opened to allow fluid to flow back into reservoir chamber 202 whereupon penile sleeve 100 returns to a non-pressurized state.

If desired, the depressurizing and further emptying of the arcuate balloons 106, 108 may be facilitated by manually squeezing penile sleeve 100 to help reverse the flow back to the reservoir.

Pressure control valve 210 may be manually opened by pressing down button 218, and it will automatically open when arcuate balloons 106, 108 exceed a predetermined level. Pressure control button 218 transmits force to a flexible membrane portion 232 of the pressure control housing 234 to cause sealing disengagement. As a result, fluid flows from pressurized arcuate chambers 106, 108 to reservoir 202 through bypass conduit 222. When the deflecting pressure on the membrane portion of the pressure control housing is removed, a preloaded spring (not shown) restores the sealing arrangement, cutting off flow through bypass conduit 222. Other pressure control valves known to those skilled in the art may also be used.

Pressure control valve 210 may also serve as a safety valve for penile sleeve 100. When the fluid pressure in arcuate balloons 106, 108 exceeds a predetermined safe pressure, fluid flows back from the arcuate balloons to reservoir chamber 202 through bypass conduit 222 until a safe pressure is reached whereupon pressure control valve 210 resumes its fluid tight sealing arrangement.

Reservoir 202 serves primarily as a distensible chamber for pressurized fluid from the arcuate balloons and is sized accordingly (3-6 cc). The exact dimensions of arcuate balloons 106, 108, and reservoir 202 are not critical as long as they are adequate to provide their intended function. The reservoir wall is preferably a resilient and compliant balloon of any elastomeric material such as silicone. Silicone rubber is preferred because it is quite resistant to wear and remains functional for long periods of time. However, other suitable materials possessing desirable properties may also be employed.

FIG. 19 is a side view of penile sleeve 100 installed over the base of penis 240. A narrow air gap 242 is present between the inner margin of sleeve 100 and the skin surface of the penis. However, there is a tight fit at the more elastic distal portion. As will be illustrated hereinafter, air gap 242 will be eliminated upon inflation of arcuate balloons 106, 108 after a partial vacuum has been generated in the vacuum chamber.

Figure 20A:
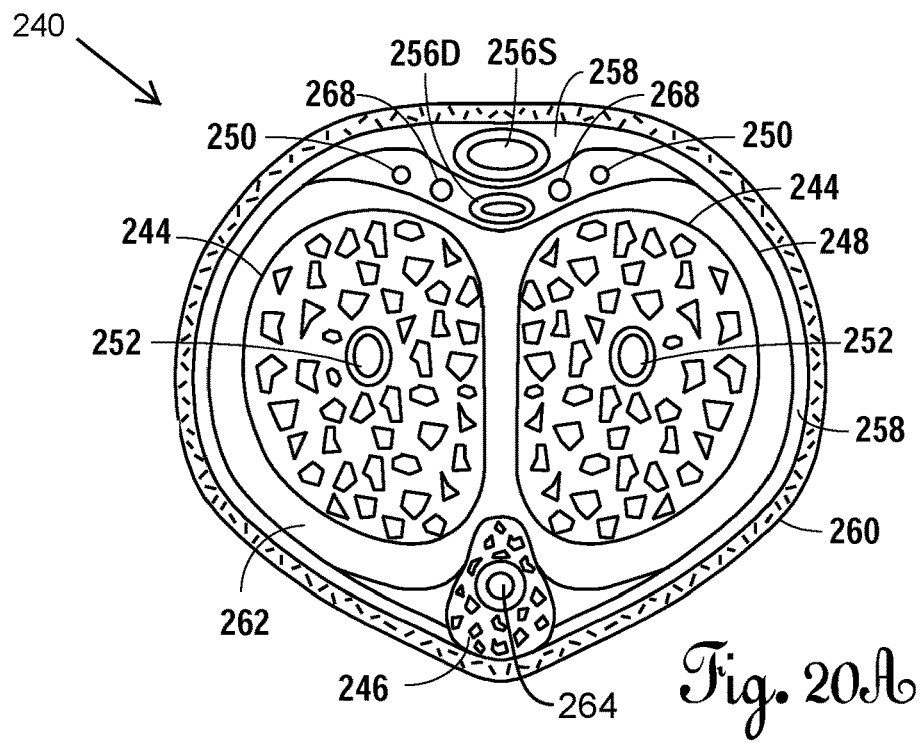
FIG. 20A is a schematic view of portion of a human penis and FIG. 20B is an anatomical cross-sectional view of a human penis taken along the axial plane 20B-20B of FIG. 20A.
Figure 20B:
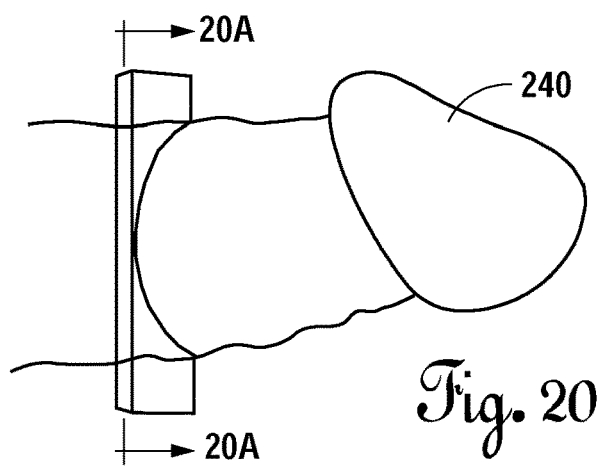

FIG. 20A is an anatomical cross-sectional view of the penile shaft taken in the axial plane 20A-20A of penis 240 shown in FIG. 20B. The penile shaft is composed of three erectile columns, the two corpora cavernosae 244, and the corpus spongiosum 246, as well as the columns enveloping fascial layers 248, nerves 250, cavernosal arteries 252, veins 256, dorsal arteries 268, and lymphatics (not shown), all covered by areolar tissue 258 and skin 260.

The tunica albuginea 262 becomes thicker ventrally, where it forms a groove to accommodate corpus spongiosum 246. Tunica albuginea 262 of the corpus spongiosum is considerably thinner (less than 0.5 mm) than that of corpus cavernosae 244, (approximately 2 mm). The cut surface of the corpora cavernosae 244 looks like a sponge.

Blood flow to the corpora cavernosae 244 is via the paired deep arteries 252 of the penis (cavernosal arteries), which run near the center of each corpus cavernosum 244.

Corpus spongiosum 246 lies in the ventral groove between the two corpora cavernosae 244. The urethra 264 passes through corpus spongiosum 246. Corpus spongiosum 246 possesses a much thinner and more elastic tunica albuginea to allow for distention of the corpus spongiosum for passage of ejaculate through the urethra. The distal extension of the corpus spongiosum 246, the glans penis 266 covers the distal tips of the corpora cavernosa 244 to provide a cushioning effect.

On the dorsal aspect of the corpora cavernosa 244, the superficial and deep dorsal veins 256S, 256D and paired dorsal arteries 268 and branches of the dorsal nerves 250 are contained within the deep penile (Buck) fascia 248. This fascia splits to surround the corpus spongiosa, and it extends into the perineum into the deep fascia of the ischiocavernous and bulbospongiosus muscles. The deep penile (Buck) fascia 248 encloses these muscles and each crus of the corpora cavernosae and the bulb of the corpus spongiosa adhering these structures to the pubic and ischial bones and to the urogenital diaphragm.

Figure 21:
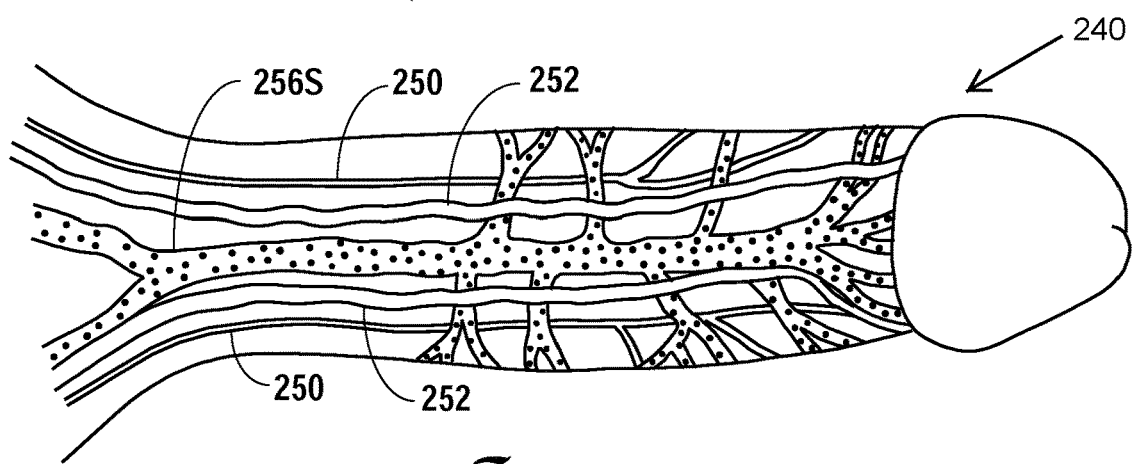
FIG. 21 is a perspective top elevational anatomical view of a human penis showing anatomy of dorsal penile veins, arteries, and nerves.
Figure 22A:
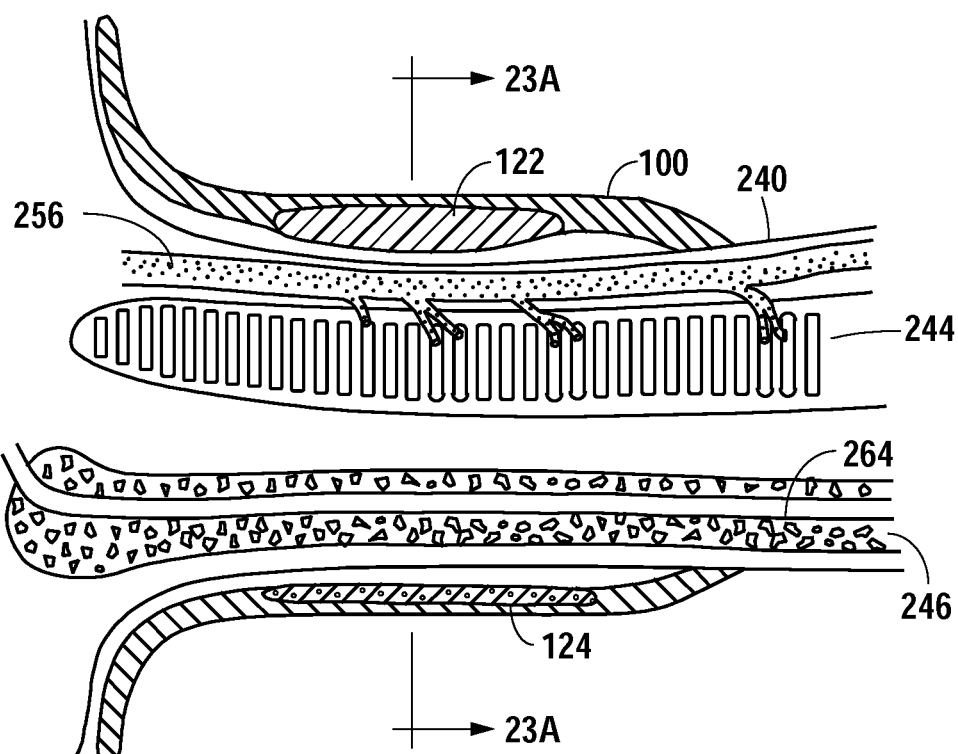
FIGS. 22A and 22B are schematic cross-sectional view of penile sleeve encircling a penile shaft taken along the line 22-22 of FIG. 19 prior to and after arcuate balloon inflation.
Figure 22B:
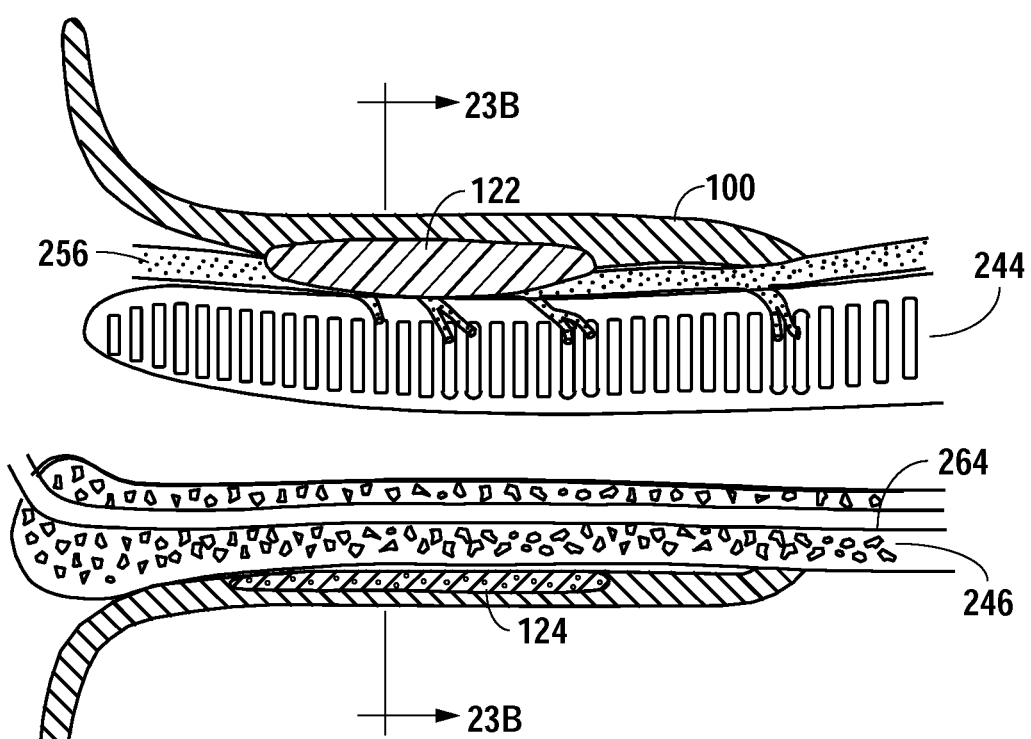
Figure 23A:
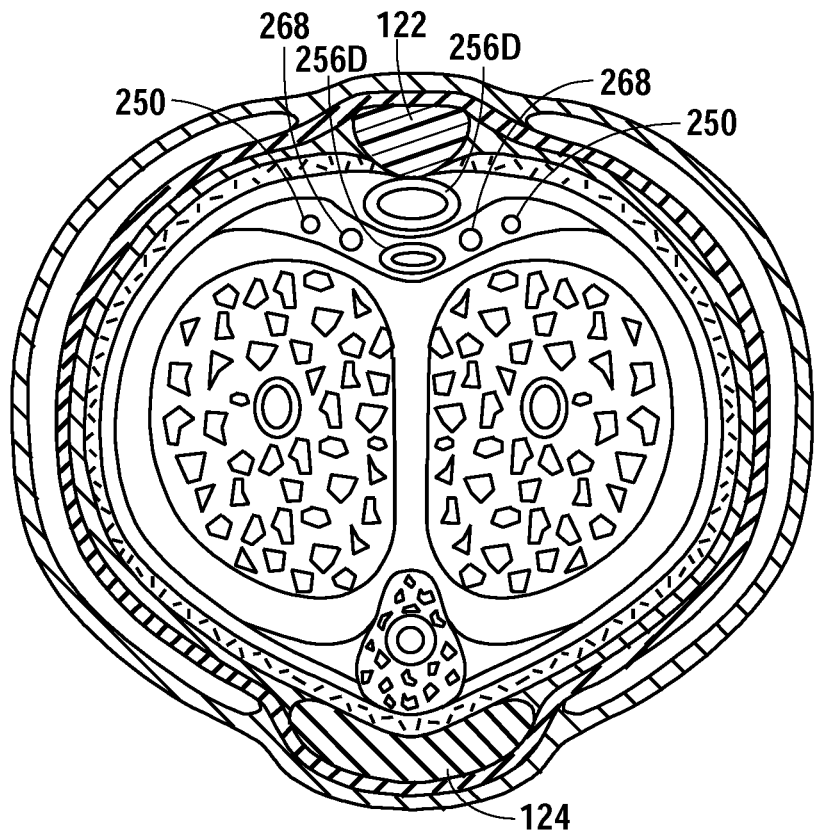
FIGS. 23A and 23B are anatomical cross-sectional views taken in the sagittal plane of a penile shaft within the penile sleeve prior to and following inflation of the arcuate balloons, respectively.
Figure 23B:
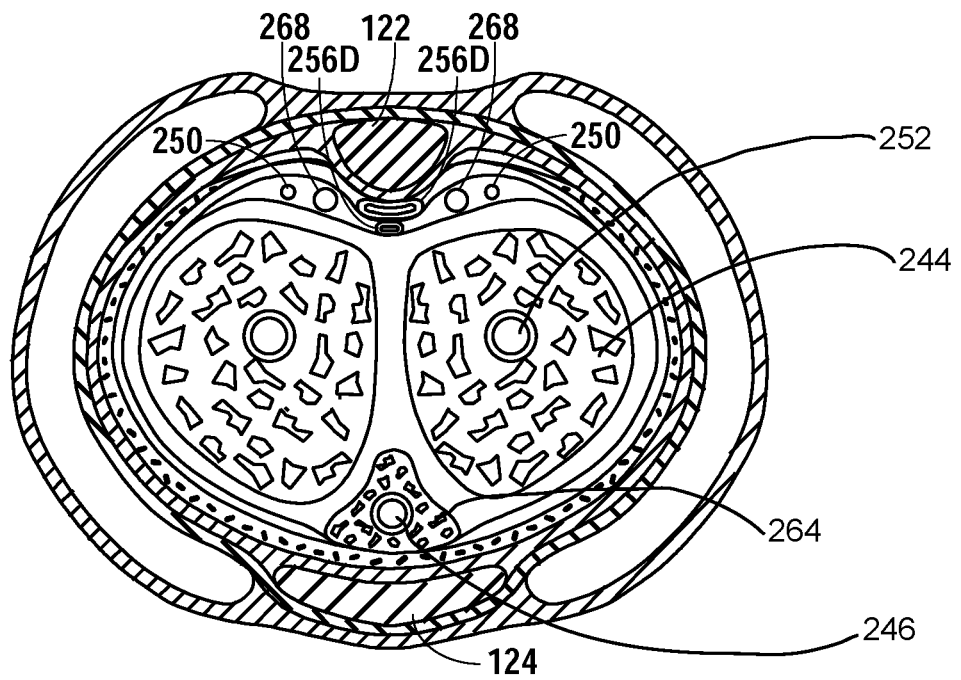

FIG. 21 is a top view showing the anatomy of penis 240. FIG. 22A shows penile sleeve 100, applied around the shaft of the penis 240. As demonstrated, the wedge-shaped dorsal insert 122 of penile sleeve 100 is critically positioned adjacent the penile dorsal veins 256, medial to the dorsal penile arteries and nerves. Likewise, ventral insert 124 is positioned and configured to act as a soft cushioning truss to urethra 264 and surrounding corpus spongiosum 246. Arcuate balloons 106, 108 are configured to provide lateral support to corpora cavernosae 244 similar to the tunica albuginea 262. When inflated, arcuate balloons 106, 108 expand somewhat analogous to the engorgement of the corpora cavernosae 244, and are constrained by fiber matrix 130 similar to the constraining action of the tunica albuginea 262.

It may be appreciated that the overall design of penile sleeve 100 mimics many anatomical features of the normal human penis. To maximize the effectiveness of any prosthesis, it is desirable that the prosthesis have characteristics which closely resemble that of the tissue or organ it is augmenting. Accordingly, the overall design of penile sleeve 100, including the selection and use of polymeric materials, relationship of textile polymeric substrates, inflatable or expandable spaces, and their proximity to or opposition to anatomical structures within the penis has aimed at fitting form to function. Thus, penile sleeve 100 is an ordered hierarchical composite structure utilizing biomimicry to augment the natural function of a normal human penis.

The inner and outer layers of penile sleeve 100 comprise a soft silicone material that feels like soft human skin. The inflatable and expandable arcuate chambers are configured to resemble engorgement of the corpora cavernosae and corpora spongiosum during a normal erection. Under internal pressure, fiber matrix 130 restricts the expansion of the cylindrical collar and provides it with relative rigidity, similar to the action of the tunica albuginea 262 and Buck fascia 248 of the penile shaft. The selection of durometers of different components, and the position and elasticity of fiber matrix 130 are configured to provide constraining and/or expansion functions similar to normal tissues present in the penis.

The increased support and rigidity provided by fiber matrix 130, when stretched by arcuate balloon inflation, to penile sleeve 100 (and to the penile shaft therein), and to skirt 116 portion resting firmly against the groin is similar to the function of the deep penile (Buck) fascia as it anchors the base and root of the penis to the pubis, ischium, and the urogenital diaphragm.

Referring to FIGS. 22A, 22B, 23A, and 23B, as the arcuate balloons are inflated, stretching of fiber matrix 130 and ventral insert 124 provide a constraining effect causing inward depression of dorsal insert 122. There is also decrease in the dorsal to ventral dimension. Most notably, the depression of dorsal insert 122 causes flattening and compression of the dorsal penile veins, sparing the dorsal penile arteries 268 and nerves 250 because of its wedge-shaped configuration.

There is elongation of the ventral insert 124 providing a cushioning effect on corpus spongiosum 246 and urethra 264. Blood flow within deep penile arteries 252 remains essentially uncompromised. Corpora cavernosae 244 and corpus spongiosum 246 remain engorged and distended during the state of penile erection, and maintain mechanical support to the root of the penis, with enhanced dimensional stability by the firm and expanded penile sleeve 100.

Figure 24:
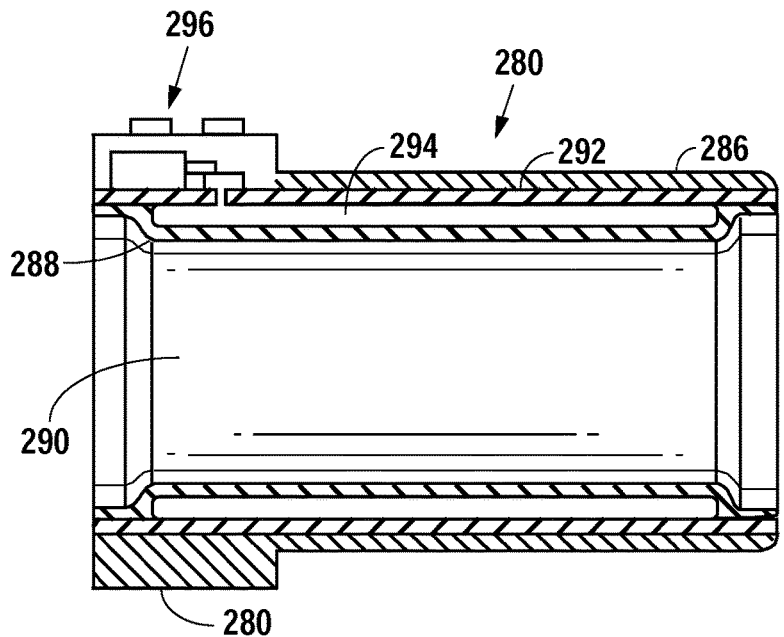
FIG. 24 is a cross-sectional view of one embodiment of an inflatable sealing apparatus.
Figure 25:
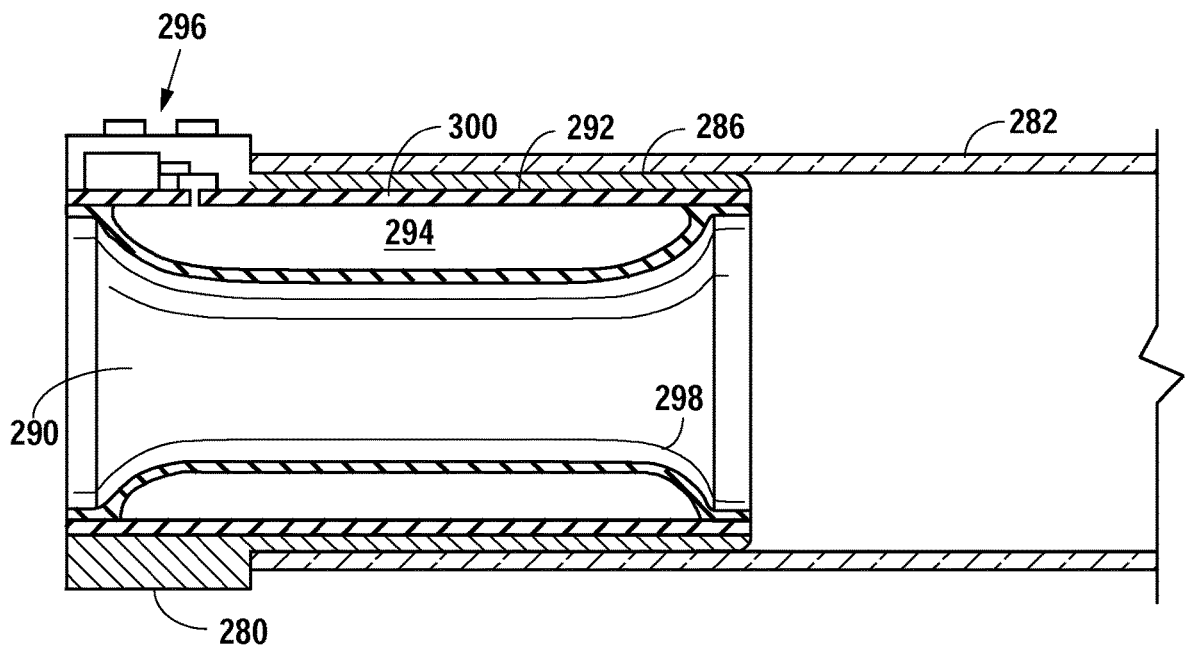
FIG. 25 is a top elevational view of the inflatable sealing apparatus that has been telescopically introduced in the frontal end of a vacuum erection tube.

Referring to FIGS. 24-26, an inflatable sealing apparatus 280 is configured to provide a substantially airtight seal around penile sleeve 100, to draw the penis into a vacuum chamber 282 so that a satisfactory erection is achieved; penile sleeve 100 is then pressurized to maintain the erection after the inflatable sealing apparatus and vacuum tube are removed.

Inflatable sealing apparatus 280 can be provided as a kit containing a cylindrical vacuum chamber 282 with inflatable sealing apparatus 280 received telescopically in the inlet 284 of vacuum chamber 282, and with a hand or power operated pump at the outlet of vacuum tube 282.

Sealing apparatus 280 may comprise a generally cylindrical housing 286 having an inlet 288 and a penile sleeve 100 receiving chamber 290. Cylindrical housing 286 is composed of a rigid tubular element 292 which is preferably transparent, having an inner pressurizable chamber 294 that provides a diaphragm seal between device 280 and penile sleeve 100.

Along the proximal outer margin of cylindrical housing 280, an inflation-deflation unit 296 is provided in the form of a small chamber comprising a fluid reservoir, at least one valve, and a pumping mechanism for transferring fluid to and from the annular pressurizable chamber 294. The volumetric capacity of the reservoir is in the order of 5-10 cc.

Referring to FIG. 24, annular pressurizable chamber 294 is in a deflated state and penile sleeve 100 receiving chamber 290 is wide open to accommodate a standard size penile sleeve 100. FIG. 25 illustrates inflation of the annular chamber 294. The pressurizable fluid is preferably a sterile liquid such as saline.

The distensible body portion of inflatable sealing apparatus 280 may be formed from an elastomeric material that may be thermoplastic or thermoset. An inner layer 298 and an outer layer 300 may be formed from two concentric round tubes. The outer layer is sized to be received along the inner margin of the housing and securely bonded thereto. The annular edges of the first and second concentric round tubes are aligned and bonded together, thus creating a fluid tight annular space there between. The annular edges may be joined by means such as gluing, welding, or by RF energy.

Figure 26A:
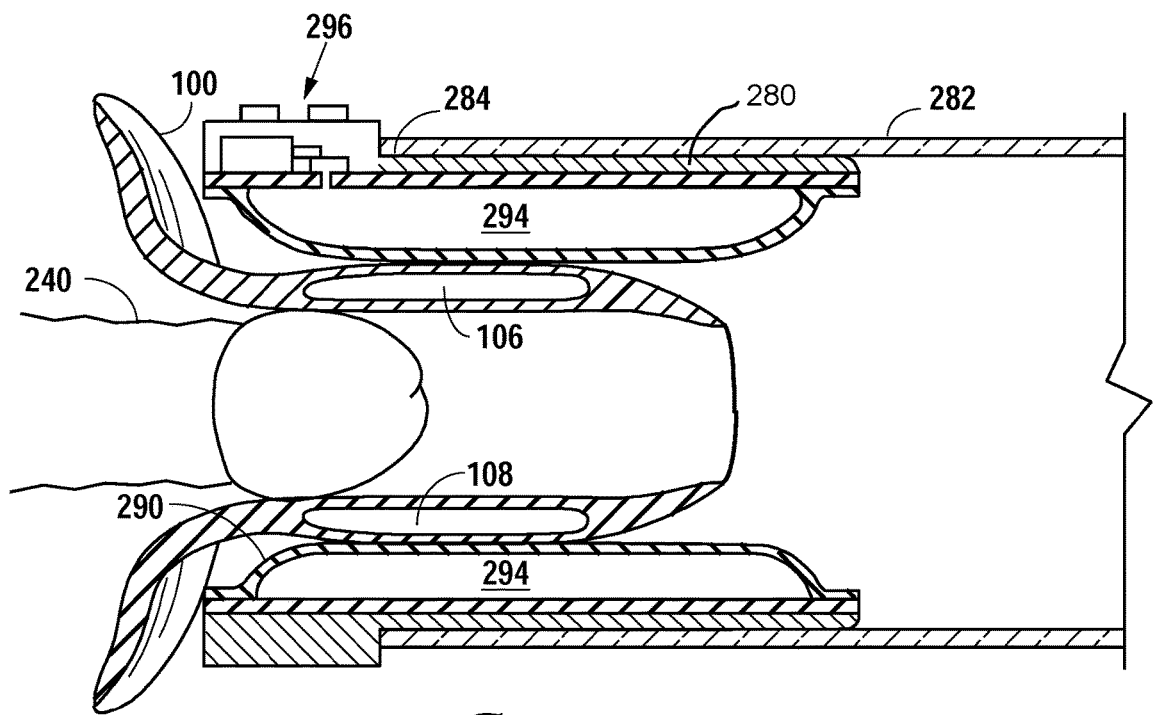
FIG. 26A is a top elevational view of the inflatable sealing apparatus shown in FIG. 24 following insertion of penile sleeve and the glans of a flaccid penis, and the proximal aperture of the sleeve prior to application of vacuum pressure in an evacuation tube.

FIG. 26A illustrates penile sleeve 100 placed in the inlet of inflatable sealing apparatus 280, and annular pressurizable chamber 294 is partially inflated. An airtight seal is formed between the outer surface of penile sleeve 100 and the diaphragm seal of pressurizable chamber 294. When the glans of a flaccid penis 240 is placed in the proximal aperture of penile sleeve 100 and the vacuum chamber 282 is activated, the decrease in pressure inside the chamber draws the penis into the cylindrical portion of penile sleeve 100 as demonstrated in FIG. 26B. If an air leak develops between the inner surface of penile sleeve 100 and the penis, arcuate balloon inflation may be activated by the user utilizing the pump button. A small amount of gel lubricant to the outer surface of the penis and to the outer surface of penile sleeve 100 may improve the effectiveness of the seal. By inflating the arcuate balloons 106, 108 within penile sleeve 100, the increase in the outer diameter of the sleeve produces an airtight seal between penis 240 and penile sleeve 100, and between penile sleeve 100 and annular pressurizable chamber 294. By such engagement, the air gap between the sealing member and penile sleeve 100 is eliminated to minimize any air leak through this space; thus providing a mechanism for achieving appropriate high vacuum pressure without possibility of an air leak.

Conventional penile inflation devices achieve about 15 inches of mercury of vacuum pressure, while a satisfactory and usable erection often requires about 20 inches of mercury of vacuum pressure. Inflation of annular pressurizable chamber 294 of inflatable sealing apparatus 280 and the arcuate balloons 106, 108 of penile sleeve 100 is kept to a minimum to maintain an airtight seal until a satisfactory erection is achieved, as judged by the user. If the user is able to tolerate the degree of negative pressure and/or maintain the pressure at a certain level as further enlargement of the penis observed, the root of the penis, which extends inwardly of the groin of the individual, is drawn into penile sleeve 100, and thus maintained in an engorged state, and stabilized by penile sleeve 100.

When the user is satisfied with the degree of erection, further fluid is pumped into arcuate balloons 106, 108 until a firm and secure grip at the root of the penis and the base of the penis is achieved and adequate pressure is exerted on dorsal penile veins 256S and 256D by dorsal insert 122. The pressurized chamber of the inflatable sealing apparatus is then deflated, and the vacuum tube is removed.

FIG. 26A shows inflatable sealing apparatus 280 slid into position within the inlet of vacuum tube 282. Penile sleeve 100 has been applied to a flaccid penis, and slid into penile sleeve 100 receiving chamber 290. By inflating fluid into the fluid tight annular chamber 294, a localized constrictive engagement between the sealing member and the outer surface of penile sleeve 100 is facilitated. By inflation of the arcuate balloons within penile sleeve 100, outward increased diameter of the sleeve produces an airtight seal between the penis and penile sleeve 100, and between penile sleeve 100 and the inflatable sealing apparatus. By such engagement, the outer open space between the sealing member and penile sleeve 100 is obliterated thus preventing any air leak through this space into the vacuum chamber.

In use, males who are able to spontaneously produce an erection but cannot physiologically maintain it, penile sleeve 100 may be of benefit in reliably and conveniently applying even pressure on the dorsal penile veins as explained previously. Thus, penile sleeve 100 obviates the inconvenience and disadvantages of conventional constriction bands and other existing constriction devices.

Figure 27A:
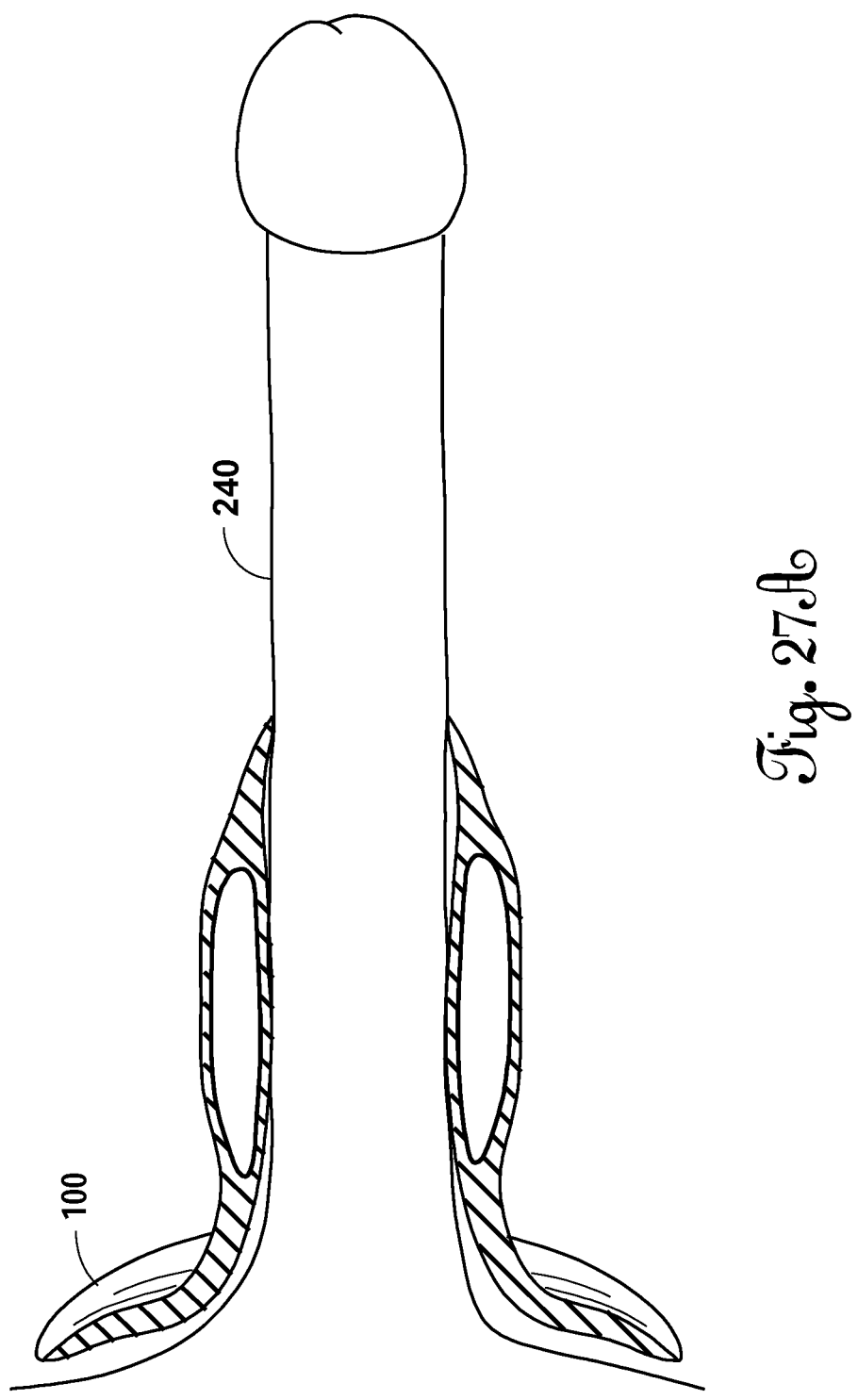
FIG. 27A is a top elevational view of the pressurized penile sleeve encircling the base of the erect penis.

In such applications, the deflated sleeve 100 is positioned about the erect penis 240 as depicted in FIG. 27A; and is subsequently inflated and expanded by repeatedly pressing pump button 216 until a snug fit is obtained.

In an alternative method of use, in patients who are unable to achieve a spontaneous erection or maintaining it physiologically, application and removal of penile sleeve 100 may be aided by the use of inflatable sealing apparatus 280.

Figure 26B:
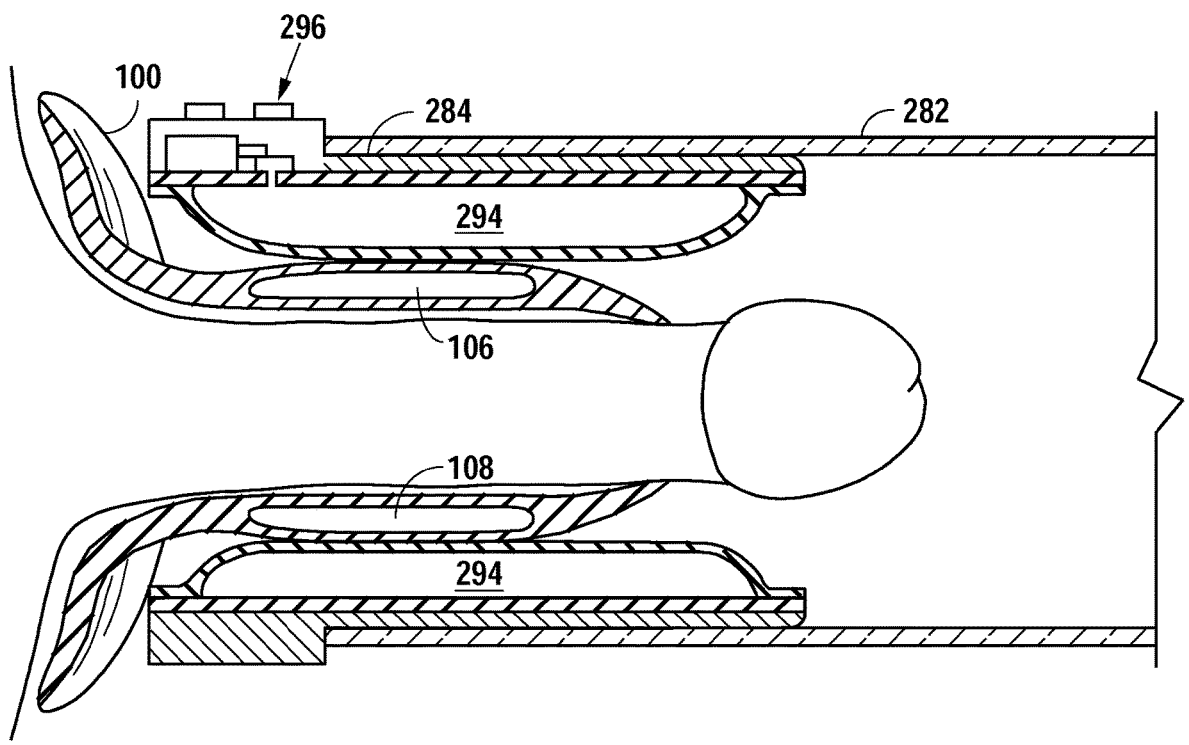
FIG. 26B is a top elevational view similar to FIG. 26A taken following activation of vacuum pressure in the vacuum chamber, showing suction and advance of the flaccid penis into the cylindrical collar portion of penile sleeve.

Referring to FIGS. 26A, 26B and 26C, inflatable sealing apparatus 280 has been coupled to vacuum chamber 282. Annular chamber 294 of inflatable sealing apparatus 280 is flat and in a deflated state. Penile sleeve 100 is placed into the inlet opening of inflatable sealing apparatus 280, the annular chamber 294 is inflated slightly until it contacts the outer margin of the still deflated penile sleeve 100. The user may be able to visualize this process through the transparent wall of the device. Subsequently, the users flaccid or semi-flaccid penis 240 is placed into the entry end of penile sleeve 100, at the proximal funnel-like aperture. The vacuum pump is then activated to begin drawing air out of vacuum chamber 282. This causes the penis 240 to be drawn into the inflatable sealing apparatus as shown in FIG. 26B. Initially, only minimal vacuum is needed to draw the relatively flaccid penis into penile sleeve 100 and into the vacuum device; the contact surface is sufficient to provide an airtight seal. This seal enables the pump to obtain an intermediate amount of vacuum pressure inside vacuum chamber 282. This intermediate amount of vacuum pressure causes the penis to begin engorging and begin to draw the base of the penis 240 further into penile sleeve 100, until skirt 116 abuts the groin.

When a sufficient amount of penile engorgement has been achieved, the user may inflate arcuate balloons 106, 108 by repeatedly manually depressing pump button 216 of inflation-deflation unit 200. As arcuate balloons 106, 108 are further pressurized, the sleeve expands radially outward, and a more secure airtight seal is achieved between the outer margin of penile sleeve 100 and inflatable annular chamber 294 of inflatable sealing apparatus 280 Penile sleeve 100 also expands radially inward to compress tightly about the base of the penis 240, minimizing the air gap shown in FIG. 19.

As described previously, pressurized inflation of arcuate balloons 106, 108 is accompanied by a localized constrictive action by the wall of penile sleeve 100 and/or fiber matrix 130 that depresses dorsal insert 122 into a specifically localized portion of the dorsa of the penis 240, which provides localized flattening and compression of the dorsal penile veins.

A higher level of vacuum suction may be applied at this time, if desired, as shown in FIG. 26C to induce an increased level of penile distention and rigidity. When a sufficient amount of constriction has been applied, pressure control valve 210 and check valve 208 hold the pressure within chambers 106, 108 of penile sleeve 100 so that an erection is maintained.

The user then deflates annular chamber 294 of inflation-deflation unit 280 and pressurized penile sleeve 100 with the erect penis therein are then withdrawn from the inflatable sealing apparatus.

Referring now to FIGS. 27A, 27B, and 27C, penis 240 is shown in various degrees of erection, when the erect penis is out of the vacuum chamber, the user may elect to further increase the degree of arcuate balloon inflation in order to augment cephalad curvature of the shaft of the penis and further increase dynamic stability of the base of the penis if needed. As discussed above, this cephalad curvature augmentation option is provided by the curvature control arrangement of the penile system design of the present disclosure. When the user no longer desires an erect penis, pressurized penile sleeve 100 may be deflated by activating pressure control button 218. More complete deflation of penile sleeve 100 may be achieved by the user manually squeezing penile sleeve 100, and the deflated sleeve can then be removed.

The invention claimed is:

1. A penile erection system comprising:
  a tubular penile sleeve formed of soft elastomeric material having dimensions expandable to accommodate a flaccid or erect penis, the tubular sleeve having a ventral side, a dorsal side, two lateral sides, a substantially funnel-shaped proximal end, and a tapering distal end;

a pair of arcuate balloons embedded in the sides of the penile sleeve;

a dorsal insert on the dorsal side of the penile sleeve, said dorsal insert configured to apply pressure to the dorsal veins of an erect penis;

a ventral insert on the ventral side of the penile sleeve; and a fiber matrix embedded in said penile sleeve.

2. The penile erection system of claim 1, wherein the fiber matrix comprises a woven or knitted fabric in which the threads extending in a circumferential direction versus a longitudinal direction have variable compliance to control curvature of the penile sleeve.

3. The penile erection system of claim 1, wherein said arcuate balloons have inner and outer curved walls and distensible chambers, wherein, when inflated with a non-compressible fluid, said arcuate balloons distend so said inner curved wall is displaced inwardly and said outer curved wall is displaced outwardly with respect to a central axis of said penile erection system.

4. The penile erection system of claim 3, wherein said inward displacement of said inner curved wall provides mechanical support to a base of a penis during an erection.

5. The penile erection system of claim 3, wherein said inward displacement of said inner curved wall eliminates an air gap between an outer surface of a penis and said penis sleeve to create a substantially airtight seal.

6. The penile erection system of claim 1, wherein inflation of said arcuate balloons causes said dorsal insert to translate ventrally to compress said dorsal penile vein and impede venous return from said organ to induce or maintain an erection.

7. The penile erection system of claim 6, wherein ventral displacement of said dorsal insert avoids undue compression of said dorsal penile arteries and nerves.

8. The penile erection system of claim 1, wherein said ventral insert comprises a soft and compliant elastomeric material that is shaped and configured to provide increased circumferential elasticity to said sleeve and to avoid undue compression of said urethra.

9. The penile erection system of claim 1, wherein pressurized inflation of said arcuate balloons causes said penile erection system to assume a predetermined curved configuration in the longitudinal direction so that it is configured to deflect a distal penile shaft and glans cephalad.

10. The penile erection system of claim 1 further comprising a skirt portion coupled to the penile sleeve, wherein the skirt portion is tailored to fit snugly against said users groin.

11. The penile erection system of claim 1, further comprising a fluid transfer apparatus for supplying pressurizing fluid to said arcuate balloons of said penile sleeve.

12. The penile erection system of claim 11, wherein said fluid transfer apparatus comprises a pressure control valve for quickly equalizing pressure between a reservoir and said arcuate balloons.

13. The penile erection system of claim 1, further comprising an inflatable sealing apparatus adapted to sealingly receive said penile sleeve.

14. The penile erection system of claim 13, wherein inflation of said arcuate balloons eliminates any air gap between an outer surface of said penile sleeve and an inner surface of said inflatable sealing apparatus.

15. The penile erection system of claim 13, wherein said inflatable sealing apparatus comprises a cylindrical tubular housing with an inflation-deflation unit located at an inlet thereof, the inflation-deflation unit adapted to eliminate any air gap between said penile sleeve and an inner surface of the inflatable sealing apparatus.

16. A method of enhancing and maintaining a physiologic condition of a male erection comprising:

positioning a penile sleeve according to claim 1 over an erect penis of a user;

pressurizing arcuate chambers in said penile sleeve to apply pressure to said penis to maintain said penis in an erect state.

17. The method of claim 16, wherein the step of pressurizing the arcuate chambers comprises manually pumping a quantity of pressurized fluid into said arcuate balloons.

18. A method of initiating and maintaining erection of a flaccid penis comprising:

providing an inflatable sealing apparatus attached to a cylindrical vacuum erection device;

positioning a penile sleeve according to claim 1 into an inlet of said inflatable sealing apparatus;

positioning a user's flaccid penis into said penile sleeve;

activating a fluid transfer apparatus to partially pressurize arcuate balloons of said penile sleeve to create a fluid tight seal between said sleeve and said penis;

activating an inflation-deflation unit of said inflatable sealing apparatus to create a substantially fluid tight seal between said inflatable sealing apparatus and said penile sleeve;

activating an evacuation cycle of the cylindrical vacuum erection device to create a partial vacuum to draw said flaccid penis into said penile sleeve until said user has achieved a desired erect state;

further pressurizing the arcuate balloons of said penile sleeve to obtain adequate compression of a user's dorsal penile veins;

releasing said partial vacuum created by said evacuation cycle;

deactivating the inflation deflation unit of said inflatable sealing apparatus to deflate said inflatable sealing apparatus;

withdrawing said erect penis and said pressurized penile sleeve from said inflatable sealing apparatus.

* * * * *